United States Patent [19]

Zacoi

[11] Patent Number: 5,072,875
[45] Date of Patent: Dec. 17, 1991

[54] APPARATUS FOR CONTROLLING THE TEMPERATURE OF AN AREA OF THE BODY

[75] Inventor: Thomas N. Zacoi, Pittsburgh, Pa.

[73] Assignee: Federal Leasing Rehab Company, Pittsburgh, Pa.

[21] Appl. No.: 493,932

[22] Filed: Mar. 15, 1990

[51] Int. Cl.$^5$ ............................................. A61F 7/00
[52] U.S. Cl. ................................. 128/400; 128/402; 128/380; 128/382
[58] Field of Search ............... 128/400, 402, 399, 379, 128/380; 165/46

[56] References Cited

U.S. PATENT DOCUMENTS

| | | | |
|---|---|---|---|
| 1,860,847 | 5/1932 | Armstrong | 128/402 |
| 3,463,161 | 8/1969 | Andrassy | 128/402 |
| 3,674,034 | 7/1972 | Hardy | 128/379 |
| 3,815,610 | 6/1974 | Winther | 123/380 |
| 3,822,705 | 7/1974 | Pilotte | 128/379 |
| 3,867,939 | 2/1975 | Moore et al. | 128/400 |
| 3,871,376 | 3/1975 | Kozak | 128/403 |
| 3,882,873 | 5/1975 | Arango | 128/379 |
| 3,905,367 | 9/1975 | Daplich | 128/254 |
| 3,995,621 | 2/1976 | Fletcher et al. | 128/2 H |
| 4,026,299 | 5/1977 | Sauder | 128/400 |
| 4,033,354 | 7/1977 | De Rosa | 128/379 |
| 4,042,803 | 8/1977 | Bickford | 219/211 |
| 4,081,150 | 3/1978 | Tyson | 128/402 |
| 4,107,509 | 8/1978 | Scher et al. | 219/211 |
| 4,114,620 | 9/1978 | Moore et al. | 128/254 |
| 4,149,541 | 4/1979 | Gammons et al. | 128/400 |
| 4,202,325 | 5/1980 | Villari et al. | 128/24 R |
| 4,335,726 | 6/1982 | Kolstedt | 128/400 |
| 4,338,944 | 7/1982 | Arkans | 128/400 |
| 4,372,318 | 2/1983 | Viesturs et al. | 128/403 |
| 4,459,468 | 7/1984 | Bailey | 219/490 |
| 4,470,417 | 9/1984 | Gruber | 128/402 |
| 4,523,594 | 6/1985 | Kuznetz | 128/402 |
| 4,527,566 | 7/1985 | Abare | 128/402 |
| 4,556,055 | 12/1985 | Bonner | 128/821 |
| 4,585,003 | 4/1986 | Meistrell | 128/402 |
| 4,586,506 | 5/1986 | Nangle | 128/403 |
| 4,614,189 | 9/1986 | Mackenzie | 128/380 |
| 4,688,572 | 8/1987 | Hubbard et al. | 128/402 |
| 4,736,088 | 4/1988 | Bart | 219/211 |
| 4,742,827 | 5/1988 | Lipton | 128/380 |
| 4,753,240 | 6/1988 | Sparks | 128/379 |
| 4,753,241 | 6/1988 | Brannigan et al. | 128/380 |
| 4,846,176 | 7/1989 | Golden | 128/400 |
| 4,951,665 | 8/1990 | Schneider | 128/400 |

FOREIGN PATENT DOCUMENTS

| | | | |
|---|---|---|---|
| 0475811 | 11/1937 | United Kingdom | 128/402 |
| 2202447 | 9/1988 | United Kingdom | 128/400 |

OTHER PUBLICATIONS

"Dependable Therm-O-Rite" Advertisement—1965.
Hot/Ice Dual Function System—Revised 7/87, (4 pages).
InCare Hot/Ice System Knee Blanket Holder—Copyrighted 1989 (1 page).

(List continued on next page.)

Primary Examiner—Theatrice Brown
Assistant Examiner—Mark S. Graham
Attorney, Agent, or Firm—James L. Sherman

[57] ABSTRACT

The present invention includes apparatus for use with a temperature controlled fluid circulating device. The apparatus is for controlling a temperature of an area of a body and includes a fluid circulating blanket having first and second sides and including fluid connection hoses extending from one edge thereof and including an extended end for being connected to the fluid circulating device. A support envelope surrounds the blanket to enclose at least the first and second sides within an interior of the envelope. The support envelope includes a waterproof inside surface adjacent the first side and waterproof outside surface adjacent the second side. The waterproof inside surface has an inward layer of plastic material and outwardly disposed material for placement against the area of the body. The waterproof outside surface has an inward layer of plastic material and includes insulation material. The waterproof outside and inside surfaces of the support envelope are sealed at peripheral edges thereof to cause the support envelope to be capable of collecting fluid within the interior of the support envelope.

20 Claims, 14 Drawing Sheets

OTHER PUBLICATIONS

Thermal Power on the Spot—Copyrighted 1989 (1 page).
Cold Therapy Made Easy—Duka*Hold Compression Ice Wrap System, Copyrighted 1989 by DePuy (4 pages).
Dura*Kold Re-Usable Compression Ice Wraps Advertisement (2 pages).
Post-Op Cryotherapy and Dura*Kold—Nov. 1989 (4 pages).
Dura*Kold Hand-OUts (3 pages).
Dura*Kold Professional Prices, Jan. 1990 (1 page).
Corporate Profile (Article)—Dura*Kold (1 page).
Redi-Grip Hip Spica Support (2 pages).
Tecnol-Orthopedic Soft Goods (6 pages).
Sterling's Therapeutic Gel Wrap—Handout (2 pages).
Elasto Gel—Therapy Products (4 pages).
Derma-Cool Treatment Packs (2 pages).

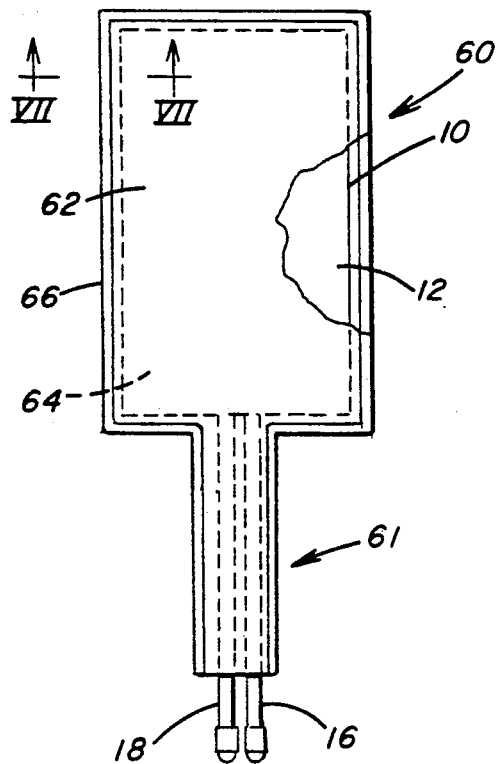
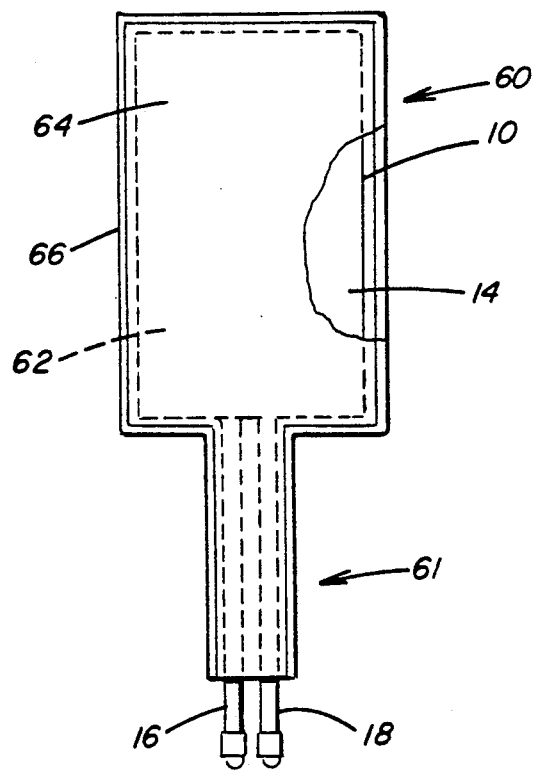
FIG. 6A  FIG. 6B
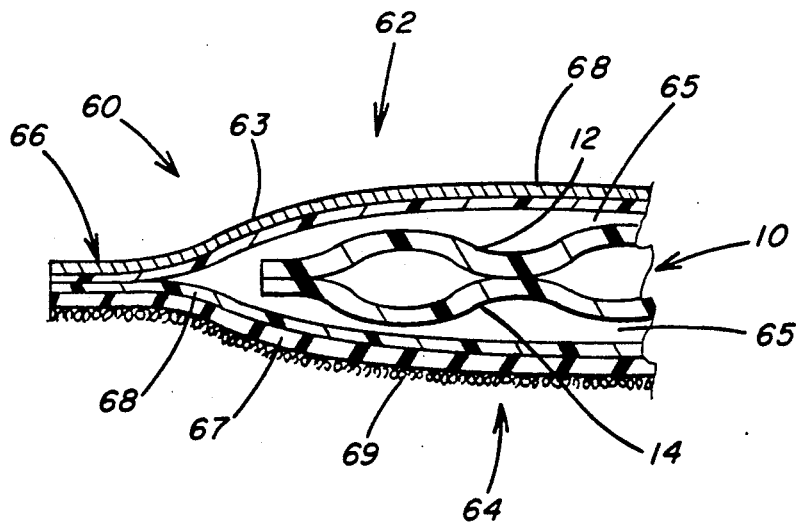
FIG. 7

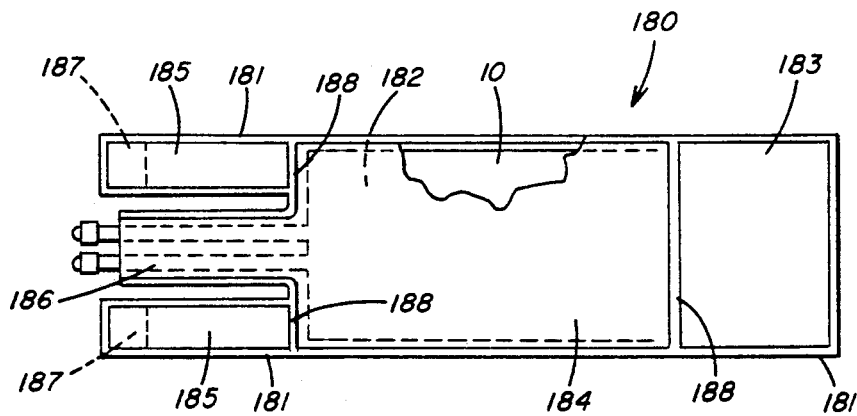
FIG. 18A
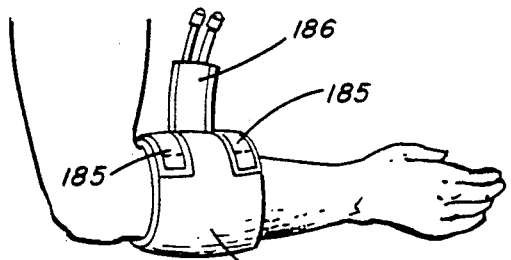
FIG. 18B
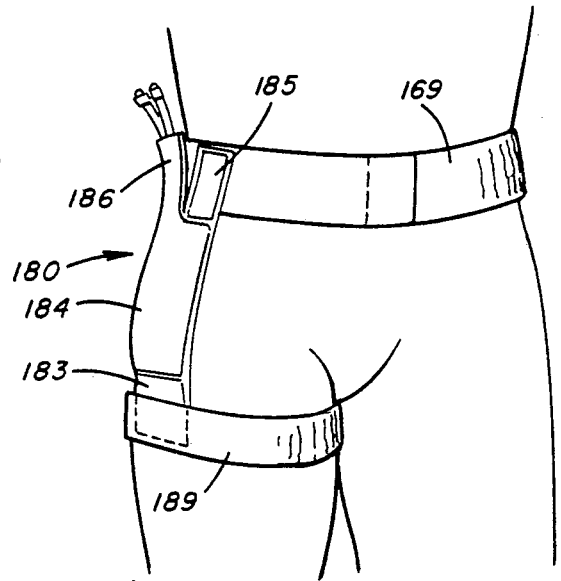
FIG. 18D
FIG. 18C
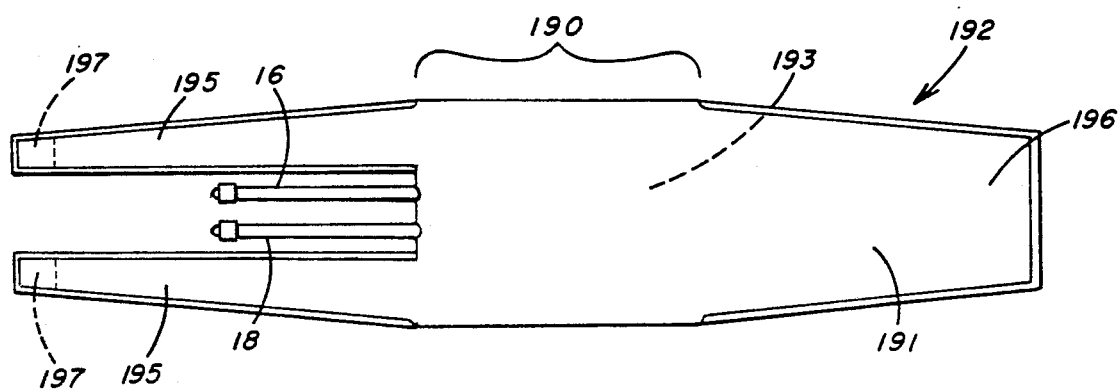
FIG. 19

APPARATUS FOR CONTROLLING THE TEMPERATURE OF AN AREA OF THE BODY

BACKGROUND OF THE INVENTION

1. Field of the Invention.

This invention relates to an apparatus for improving recovery from an injury or surgery and, more specifically, to an apparatus for controlling the temperature of an area of the body following the injury or surgery. The invention also includes the method of providing the apparatus.

2. Description of the Prior Art.

It has been found that to improve patient healing and recovery by reducing pain, swelling, and blood loss, post-operative procedures increasingly employ means for reducing the temperature in the area of the body around the surgery.

For example, after a knee operation, an ice pack or other device for reducing the temperature is applied to the area around the surgery. The area of incision, after closure, may be initially covered with a light sterile gauze. At one time, after knee surgery, the leg and knee would simply be covered with additional sterile gauze, additional sterile padding and finally wrapped from the toe to the groin with an elastic, ace bandage until the first dressing change. The ace bandage caused a compression on the leg that tended to reduce swelling and decreased the likelihood of phlebitis. Early attempts to reduce the temperature following knee surgery included applying ice packs or the like to the surface of the ace bandage in the knee area. However, the padding and bandage insulated the surgical area and made the cooling ineffective for properly reducing pain, swelling and/or blood loss.

If there were to be a means for more efficiently directing cold to the area of surgery, it would preferably be capable of extended and controlled generation of a reduced temperature. Although such a device for controlling temperature need not lie immediately against the area of incision, proper post-operative procedures require that all of the components employed in the surgical area be properly sterilized.

It would seem possible that any prior art means for holding a heat source or a cold source, such as ice, might be employed to significantly improve the likelihood that a source of cold could be maintained in a proper position on the patient. However, a number of such devices which are primarily used for therapeutic procedures have not been found to be appropriate for post-operative procedures. Some such therapeutic devices include electrical heating pads or bandages such as those disclosed in U.S. Pat. Nos. 4,042,803; 4,107,509; and 4,736,088. Some heating pad configurations employ pouch devices in which warm water or chemical substances, which combine to form heat, are installed for the therapeutic application of heat to the patient. Such devices have been disclosed in U.S. Pat. Nos. 3,815,610; 4,470,417; and 4,4742,827.

Because the preferred post-operative procedure would include means for cooling the area of the surgery, various devices, which are primarily intended to cool an area of a body, would appear to be more significant. However, some cooling devices are for use on animals rather than people. They tend to employ ice which is subject to melting or a means for directing cool liquid to the area but do not appear to have any direct application in a post-operative environment. Such devices are disclosed in U.S. Pat. Nos. 3,905,367; 3,822,705; 4,033,354; and 4,556,055.

A more extensive number of devices have been suggested for the therapeutic application of heat or cold to the human body. Such devices typically include some form of support device or wrapping device having pouches or pockets for the insertion of a hot pack or a cold pack. The cold pack may contain ice or some chemically reactive material for producing a lower temperature. Since these devices employ hot water and/or cold water or ice, the amount of time that such a device can be employed is clearly limited. The loss of heat or cold may be acceptable for therapeutic uses but is clearly undesirable for post-operative procedures. Such devices for use on various parts of the body are disclosed in U.S. Pat. Nos. 3,882,873; 4,081,150; 4,372,318; 4,586,506; 4,527,566; 4,614,189; 4,688,572; 4,753,240; and 4,753,241.

Because of the limited heating or cooling duration of the various devices discussed hereinabove, there was clearly a need for some system which is capable of applying a continuously adjustable and monitored source of heat or cold to a desired area of the body. U.S. Pat. No. 4,459,468 is directed to a temperature controlled, fluid circulating system which, perhaps, best represents the type of system which is enjoying increased acceptance in the therapeutic as well as the surgical field. This particular fluid circulating system is designed for use with a thermal blanket or pad and includes temperature controls so that both heating and cooling effects could be selectively produced through the preheating or precooling of the fluid. The fluid is pumped through the thermal blanket to provide proper heating or cooling as desired at the location of the thermal blanket. For this purpose, the thermal blanket includes supply and discharge hose means which can be conveniently coupled to and uncoupled from the overall system. For proper operation of the overall system, various sizes and shapes of thermal blankets are provided for heating or cooling different areas on the patient.

Similar fluid circulating systems are disclosed in U.S. Pat. Nos. 3,674,034; 3,995,621; 4,126,299; 4,202,325; 4,335,726; 4,338,944; and 4,523,594.

U.S. Pat. No. 3,674,034 is directed to a system for maintaining controlled deep body temperature by providing heat to efficient areas of a person's body. The system includes a series of pouches which are individually strapped to the neck, each arm pit, and each upper thigh at the groin area of a person. Each pouch consists of a cloth covered tubing array and is connected to a hypothermia machine for controlling the temperature of the body in areas where the blood arteries are close to the skin surface. Since each pouch includes a thin, low-porosity and highly thermal-conductive fabric covering the tubing array therein, efficient heat transfer is produced without burning the patient. Each of the covers is said to be removable for laundering and sterilization. However, there is no suggestion that the device could or even should be utilized in a surgically sterile area for treatment of a patient. The device disclosed in U.S. Pat. No. 3,995,621 includes a liquid cooled brassiere and is directed to a method of diagnosing malignant tumors. The device is not appropriate for nor applicable in post-operative procedures.

U.S. Pat. No. 4,202,325 is directed to a compression device having an improved fastening sleeve. The device is for applying compressive pressure against the patient's limb from a source of pressurized fluid and, again, has no post-operative application for directing heat or cold to a surgical area.

U.S. Pat. Nos. 4,335,726 and 4,338,944 disclose a therapeutic device with temperature and pressure controls. The therapeutic device includes a sleeve for covering a portion of a patient's body and has a space to receive cool circulating liquid. The device also incorporates means for applying pressure to the area of the patient to be cooled. As a result, it is recommended that this therapeutic device be used, for example, by sports trainers for the application of cold and pressure to the extremities, hands, feet, or joints of an athlete after a sprain or strain sustained during playing. Similarly, it is said that physicians in hospitals, such as emergency rooms, may employ such a device to apply cold and pressure to a patient in order accelerate healing by reducing edema and hematoma. If either such procedure were to periodically require heat, the overall therapeutic device could be readjusted for the periodic application of heat. There is no suggestion of the device being capable of being employed post-operatively.

U.S. Pat. No. 4,026,299 discloses a portable heating and cooling apparatus which utilizes flexible pads to be wrapped around a limb or other body portion of a human or animal. The portable apparatus is said to be especially useful for treating sprains, strains or other muscular injuries to athletes or race horses as soon after the injury occurs as possible in order to rapidly reduce swelling, fever or the like to the injured area. The overall system primarily employs flexible pads with a complicated array of flexible tubing loops which could be covered by a removable, non-insulating sheet which is intended to be applied to and lie against the patient's limb. This inner sheet could become soiled or worn and thus could be removed, washed or otherwise cleaned for sanitary purposes, or replaced. However, there is nothing to suggest that the apparatus would be appropriate for modern post-operative procedures which are performed on a surgically sterile environment.

U.S. Pat. No. 4,523,594 discloses a stretchable textile heat-exchange jacket. This heat-exchange jacket can be wrapped about and conform to a limb, an arm or a body member and function therapeutically to heat or cool the member. The jacket is formed of a sheet of elastic fabric material having an array of flexible plastic pipes threaded therethrough. The respective ends of the flexible pipes were coupled to an inlet fluid distributor and an outlet fluid collector. The elastic sheet is provided at its opposing sides with complimentary fabric fastener components to releasably hold the jacket securely in place on the body member even when the member is being flexed. Although this stretchable textile heat-exchanger jacket is clearly intended for therapeutic use during limited movement of a limb or joint, the general background of the invention discusses a possible use of cold following knee, leg or other surgery on an extremity where there is usually swelling in the vicinity of the incision.

U.S. Pat. No. 4,523,594 indicates that when the wound is dressed in a surgical bandage, it becomes difficult to apply ice to the site to reduce swelling and promote healing. Moreover, since surgical bandages, casts and rubberized braces used during rehabilitation are relatively impermeable to perspiration and act as thermal barriers, there is often a build-up of moisture and heat during a surgical dressing. This could create a climate conducive to bacteria. Such bacterial activity could cause infection and retard the healing process. The textile-heat exchange jacket is considered to be thin enough to be fitted under an "existing" surgical cast, bandage or brace without discomfort, whereby the jacket, when cold, could serve to reduce swelling and arrest perspiration in the wound area and also act to relive post-operative itching.

The stretchable textile heat-exchanger jacket includes a rectangular sheet of fabric woven or otherwise fabricated of elastic cotton fibers, spandex or other natural or synthetic stretchable fabric material capable of being sterilized by conventional hospital procedures. However, threaded into the fabric sheet is a parallel array of flexible pipes formed of synthetic plastic material. While the pipes are stitched into the fabric sheet, most of the tubes surfaces are exposed and engage the body member when the jacket is wrapped thereabout. Alternatively, the sheet could take the form of two superimposed plies of open-mesh, stretchable fabric, with the pipes sandwiched therebetween in a manner in which the pipes form ducts between the plies.

Despite the discussions in U.S. Pat. No. 4,523,594 regarding possible use in surgical areas, the device disclosed therein is not particularly adapted for nor appropriate for post-operative procedures. The particular heat-exchange system is clearly intended to function therapeutically to heat or cool the member and even includes a suggestion of connecting the loop system to a water faucet of a house sink which then supplies tap water to the jacket. With the confusing arrangement of tubes connected to the stretchable jacket material, the entire system has been found to be too complicated to be practically employed in an operating room and poorly configured for post-operative use.

Despite the plurality of devices discussed hereinabove, an extensive number of surgeons do not employ any means for the post-operative reduction of temperature in the surgical area. This continues to occur despite the fact, as discussed hereinabove, that temperature reduction can be more conveniently and reliably directed to a surgical area with various types of thermal blankets or pads employed in a system such as that disclosed in U.S. Pat. No. 4,459,468. The blankets are provided extended, double hoses and couplings for convenient, quick and reliable connection to the overall system. Some fluid circulating blankets or pads, such as those disclosed in U.S. Pat. Nos. 4,114,620 and 4,149,541 are primarily intended for therapeutic use but are representative of the increased interest in flexible blankets for use with such temperature controlled, fluid circulating systems. Because the temperature of the blankets can be controlled for an extended period of time with the fluid circulating system, the blankets have been used in post-operative procedures as well as the initially intended therapeutic procedures. With limited but increasing acceptance of the blankets in post-operative procedures, it is not uncommon for the thermal blankets to be pre-sterilized for use in an operating room.

Although the thermal blankets themselves are a reliable and effective source of cold, the post-operative procedures with the blankets presently being employed by surgeons are extremely complicated, time-consuming and unreliable. Typically, for example, after a knee operation, two sterilized blankets are removed from sterile packages by a nurse. The blankets are to be directed to opposite sides of the knee, adjacent the specific area of the incision. An attending nurse is also required to remove at least two pieces of 4 inch by 8 inch sterile gauze which are packed in a peel pack. One or more sterile gauze pieces are then laid on the interior surfaces of the two blankets. The nurse must then orient the double hoses which extend from each blanket towards the foot of the patient. The nurse is usually positioned toward the body side of the knee with the surgeon positioned toward the foot side of the knee. Both blankets with the gauze pieces thereon are dispose, gauze up, for eventual alignment on either side of the knee area. Next, two sterile A.B.D. pads, which are thicker and about 5 inches by 10 inches, are removed from a peel pack for application on the outer side of each of the blankets. With the gauze thereon and with the A.B.D. pads applied to the outside of each blanket, it is not uncommon for the blankets and pads to be misaligned or poorly positioned against the opposite sides of the knee area by the nurse and/or the surgeon.

With the surgeon holding the sterile gauze, blanket, and A.B.D. pad in each hand against opposite sides of the knee, the nurse begins to wrap the knee area from the thigh to below the knee with a sterile gauze roll. It is not uncommon for the surgeon's hands to be partially enwrapped or for the blankets or pads to be further misaligned as the wrapping of the gauze roll proceeds through the knee area. The double hoses extending from the bottom of the blankets must be positioned to extend outwardly of the wrapping as it continues toward the foot. As a result, the hoses of the two blankets may be at different lengths or awkwardly positioned on one side or the other of the leg to complicate eventual connection to the overall fluid circulating system.

Finally, an ace bandage is wrapped from the toe to the groin with the ends of the two double hoses again being left exposed and extending outwardly from each of the blankets in order to allow the connection to the fluid circulating system. Even the application of the ace bandage is complicated if the initial positioning and wrapping results in the blanket or the ends of the double hoses being poorly positioned.

After surgery, the blanket is normally maintained adjacent the surgical area in the manner described for as long as three to five days prior to the first dressing change. As will be seen, the first dressing change can also be significantly complicated if the blankets, etc. have not been properly positioned after the surgery. Some surgeons believe the surgical area should be cooled for up to 8 days after the surgery. At that time, the used blankets, gauze pieces, A.B.D. pads, gauze roll, and ace bandage may all be discarded as the knee continues to be treated therapeutically.

Because of the problems discussed hereinabove with positioning and maintaining the blankets in alignment with the area to be cooled, some surgeons apply sterile tape directly to the patient's body around the entire circumferential edge of the thermal blanket. Use of this much tape on the body for an extended period of time can result in a deleterious effect on the skin and, particularly, on the skin of elderly patients. Additionally, despite the normal shaving in the area of the surgery, the area to be shaved may be required to be increased because of the application of tape to the thermal blanket. Finally, eventual removal of the tape is extremely painful to many patients.

A primary objective of the invention is to present an improved method and apparatus for post-operatively controlling the temperature of the body in the area of the surgery. However, the primary benefit of such an improved method and apparatus may be the overall reduction in the time required to position and secure the thermal blankets in the operating room. During surgery, the patient is usually anesthetized. It is well known that a primary concern in surgery includes the patient's reaction to and condition when under anesthesia. Any portion of the surgery or post-operative procedure which can reduce the overall time that the patient is under anesthesia is most significant and highly desirable.

Finally, as mentioned hereinabove, a significant number of surgeons do not even attempt to control the temperature in the area of surgery during the post-operative procedure. Because of the complications encountered with the existing systems, many surgeons do not incorporate any means in the post-operative procedures for reducing the temperature in the area of surgery. This occurs despite the clear indication that reducing the temperature in the area of the surgery can reduce the pain, swelling, blood loss of the patient and significantly reduce the time required for the patient to stay in the hospital. As a result, any means which can increase the acceptance and use of the control of the temperature in the surgical area will enable surgeons and hospitals to ultimately benefit an increasing number of patients.

All of the patents discussed hereinabove are incorporated by reference as if the entire contents thereof were included herein.

OBJECTS OF THE INVENTION

It is an object of the invention to provide an apparatus which is capable or being used for post-operatively controlling the temperature in the area of a body following surgery.

It is another object of the invention to provide such an apparatus for reducing the pain, swelling, blood loss and hospital stay of the patient.

It is still another object of the invention to provide such an apparatus which can be efficiently, effectively, and reliably employed by a post-operative team.

It is still another object of the invention to provide an apparatus of the type described which will reduce the time that a patient must be anesthetized.

It is yet another object of the invention to provide an apparatus of the type described which can alternatively be conveniently and reliably used therapeutically on the body of a patient.

It is a further object of the invention to provide a preferred method of forming the apparatus of the type described.

THE SUMMARY OF THE INVENTION

These and other objects of the invention are provided in a preferred embodiment including apparatus for use with a temperature controlled fluid circulating device. The apparatus is for controlling a temperature of an area of a body and includes a fluid circulating blanket having a first side and a second side. The fluid circulating blanket has fluid connection hose means which extend from one edge thereof and include an extended end for being connected to the fluid circulating device. A support envelope surrounds the fluid circulating blanket to enclose at least the first side and the second side within an interior of the support envelope. The support envelope includes a waterproof inside surface adjacent the first side and a waterproof outside surface adjacent the second side of the fluid circulating blanket. The waterproof inside surface has means for preventing the passage of fluid therethrough and has outwardly disposed material for placement against the area of the body. The waterproof outside surface has means for preventing the passage of fluid therethrough and includes insulation material. The waterproof outside surface and the waterproof inside surface of the support envelope are sealed at peripheral edges thereof to cause the support envelope to be capable of collecting fluid within the interior of the support envelope.

The preferred apparatus includes the waterproof inside surface with an inward layer of waterproof material and an outward layer of cloth material. The inward layer and the outward layer of the waterproof inside surface are joined at least at the peripheral edges of the support envelope. The waterproof material is sheet plastic material and the cloth material is a substantially non-insulating synthetic material.

The preferred apparatus may also include the waterproof outside surface with an inward layer of waterproof material and a least one outward layer of the insulation material. The inward layer and the at least one outward layer of the waterproof outside surface are joined at least at the peripheral edges of the support envelope. The waterproof material is sheet plastic material and the insulating material is at least one of polypropylene foam material and polypropylene felt material.

The preferred apparatus also includes adjustable retaining means for retaining the support envelope on the body with the inside waterproof surface thereof against the area of the body. The adjustable retaining means includes at least one hook connection element and the waterproof outside surface of the support envelope includes surface means for being releasably connected to the at least one hook connection element. The surface means includes at least one of brushed-pile material and loop material forming an outermost layer of the waterproof outer surface. The waterproof outer surface includes an inward layer of waterproof material, an intermediate layer is between the inward layer and the outermost layer, and the intermediate layer includes the insulation material.

The support envelope may include a hose portion formed of an extension of the waterproof inside surface and an extension of the waterproof outside surface. The hose portion extends around the fluid connection hose means for support of the fluid connection hose means. The invention can include means for removing the fluid when the fluid is collected within the interior of the support envelope. The fluid circulating device and the support envelope may be sterilized.

One embodiment of the invention includes apparatus for use with a temperature controlled fluid circulating device wherein the apparatus is for controlling a temperature of an area of a body and includes a fluid circulating blanket having a first side and a second side. The fluid circulating blanket has fluid connection hose means which extend from one edge thereof and include an extended end for being connected to the fluid circulating device. The fluid circulating blanket has an elongate opening to define a first half and a second half of the fluid circulating blanket. A support envelope surrounds the fluid circulating blanket to enclose at least the first side and the second side within an interior of the support envelope. The support envelope includes an inside surface adjacent the first side and an outside surface adjacent the second side. The support envelope includes an elongated envelope opening in alignment with the elongated opening of the fluid circulating blanket. The inside surface and the outside surface are joined at least at an edge of the elongated envelope opening. There is included means for securely positioning the support envelope, with the fluid circulating blanket therein, with the inside surface of the support envelope against the area of the body.

The means for securely positioning the support envelope includes adjustable retaining means for retaining the support envelope on the body. The adjustable retaining means includes means for adjusting a width of the elongated envelope opening and the elongated opening. The means for adjusting is for selectively positioning the first half and the second half of the fluid circulating blanket in alignment with the area of the body. The inside surface and the outside surface may be waterproof and sealed at the edge of the elongated envelope opening and at a peripheral edge surrounding the fluid circulating blanket to cause the support envelope to be capable of collecting fluid within the interior of the support envelope.

The invention also includes a method of forming an apparatus for use with a temperature controlled fluid circulating device. The apparatus is for being used to control a temperature of an area of a body. The method includes the steps of: providing a fluid circulating blanket having a first side and a second side and including fluid connection hose means extending from one edge thereof, the fluid connection hose means having an extended end for being connected to the fluid circulating device; forming a support envelope around the fluid circulating blanket with at least the extended end of the fluid connection hose means extending outwardly therefrom; the forming including disposing a waterproof inside surface of the support envelope adjacent the first side and a waterproof outside surface of the support envelope adjacent the second side, the waterproof inside surface having outwardly disposed substantially non-insulating material for placement against the area of the body, the waterproof outside surface including an insulation material; and the forming including sealing the waterproof outside surface and the waterproof inside surface at peripheral edges of the support envelope to cause the support envelope to be capable of collecting fluid within an interior of the support envelope.

The method may also include in the step of forming that the support envelope includes providing an inward layer of waterproof material for each of the waterproof inside surface and the waterproof outside surface. The method further includes the step of fabricating adjustable retaining means for retaining the support envelope on the body with the waterproof inside surface against the area of the body, the adjustable retaining means including at least one hook connection element, wherein the forming of the support envelope includes providing the waterproof outside surface with an outmost layer including surface means for being releasably connected to the at least one hook connection element.

BRIEF DESCRIPTION OF THE DRAWINGS

FIG. 6A is a view of the inward side of a preferred support envelope having a fluid circulating blanket therein.

FIG. 6B is a view of the outward side of a preferred support envelope having a fluid circulating blanket therein.

FIG. 7 is a view of the preferred support envelope as seen along line VII—VII of FIG. 6A.

FIG. 18A is simplified view of another preferred support envelope for a fluid circulating blanket.

FIGS. 18B through 18D are views of the support envelope of FIG. 18A as applied to various areas of a patient.

FIG. 19 is a view of still another preferred support envelope supporting including a fluid circulating blanket area therein.

DETAILED DESCRIPTION OF THE PREFERRED EMBODIMENTS

Prior to the detailed description of the preferred method and apparatus for post-operatively controlling the temperature of an area of the body after surgery, it is appropriate to specifically discuss the existing fluid circulating blankets and some of the detailed steps which are presently required for their use in post-operative procedures.

Figure 1:
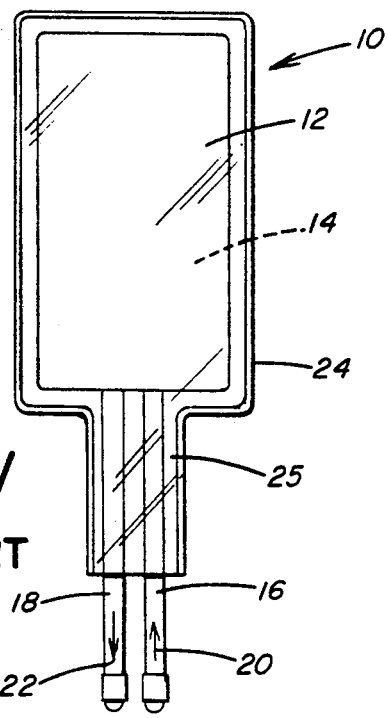
FIG. 1 is a simplified view of a typical prior art fluid circulating blanket including a plastic container thereabout.

As seen in FIG. 1, a typical fluid circulating blanket 10 would include a first side 12 and a second side 14 which are formed of sealed plastic material for retaining pressurized fluid therein. Fluid connecting hose means in the form of an inlet hose 16 and an outlet hose 18 are connected to one edge of the blanket 10. When properly connected to a temperature controlled, fluid circulating system of the type described hereinabove, cool fluid will be supplied as indicated by the arrow 20 and the warmer fluid will be a discharge as indicated by the arrow 22. The blanket 10 includes an array of internal passages or channels (not shown) for directing the fluid throughout the blanket in an effort to provide generally even heating or cooling at the first side 12.

The prior art fluid circulating blanket 10 may also include a surrounding, clear plastic container to provide a means for collecting condensation or moisture which would tend to collect on the first side 12 and the second side 14 of the fluid circulating blanket 10 during use. The plastic material of the container 24 is relatively thin and non-insulating to allow the transfer of heat or cold from the blanket to the patient. The plastic container 24, because of the thin plastic material, could only collect a limited amount of unpressurized fluid if there were any minor leaks in the fluid circulating blanket 10 after it is installed on a patient. Some such containers 24 include a hose portion 25 which extends from the major portion of the blanket 10 to also surround the hoses 16, 18.

Fluid circulating blankets 10, as shown in FIG. 1, are typically provided for both therapeutic and surgical uses. However, for surgical applications, the fluid circulating blanket 10 (including the hoses 16 and 18 and the container 24) are sterilized prior to their being used in an operating room.

Acceptable sterilization for post-operative procedures would include gamma radiation, steam heating in a steam autoclave, or, preferably, sterilizing with ETO gas (Etholene Oxide Gas). With most of the components of the preferred fluid circulating blanket 10 being formed of plastic material, steam sterilization would clearly be inappropriate and ETO gas is preferred. Prior to sterilizing, the fluid circulating blanket 10 is placed inside a package (not shown) which is then sealed. The package with the fluid circulating blanket 10 enclosed therein is placed in an ETO gas chamber for sterilization. The ETO gas completely permeates the package and the fluid circulating blanket therein. The preferred sterile package for surgery includes a double-packaging configuration. In other words, the blanket 10 is placed inside a sealed interior package which is then, in turn, placed inside a sealed exterior package. With both the interior and exterior packages being sterilized in the ETO gas, the overall configuration is less likely to be contaminated during the surgery. The exterior package can be opened in a non-sterile area with the sterile interior package being placed inside of the sterile boundary during surgery. The sterile interior package can then be opened for convenient handling of the sterilized fluid circulating blanket within the sterile surgical area.

It will be noted, during the description provided hereinbelow, that some fluid circulating blankets 10 do not include such a container 24 and those which do include a container 24 are basically positioned and used in the same manner as the overall fluid circulating blanket 10. It should also be noted that the portion 25 of the container 24 of FIG. 1 extends for some length along the hoses 16, 18. However, not all containers 24 include a portion 25 which extends as far from the major portion of the blanket 10 itself. Further, the light plastic material of container 24 at the portion 25 does not really support the hoses 16, 18 and can not be relied upon to retain them together even if it does extend for some distance from the major portion of the blanket 10.

When referring to various means for sterile packaging for the components to be described hereinbelow, reference to the package could include both an interior package and an exterior package. Unless otherwise indicated, the overall operation would not be appreciably changed whether there is a single or double packaging configuration.

Having generally explained a typical fluid circulating blanket 10 and the method of sterilizing and packaging the blanket 10, it is appropriate to describe a typical operation in which such a blanket 10 has been employed. As mentioned hereinabove, the application of cold has been advantageously employed for various types of knee surgery. Whether the surgery is total knee surgery or, for example, surgical arthroscopies including lateral release, the controlled and effective application of cold to the area reduces the pain, swelling, blood loss and the length of hospital stay of the patient.

Figure 2:
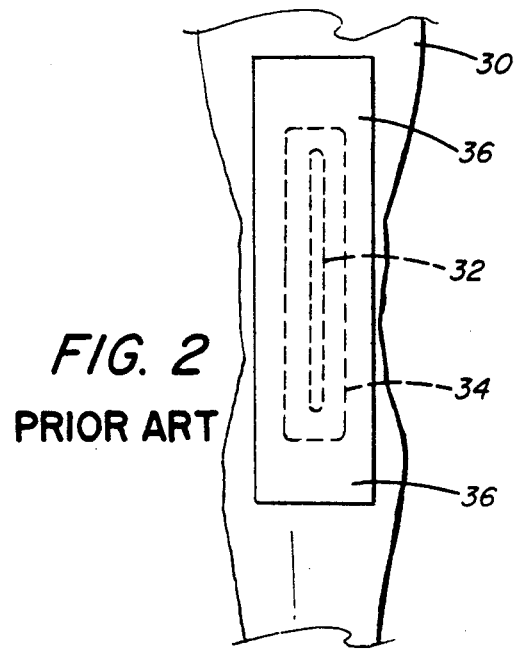
FIG. 2 is a schematic view of the typical prior art method of preparing the right knee of a patient following knee surgery.

As seen in FIG. 2, a typical knee surgery of a right leg 30 would include a mid-line incision 32. The incision 32 is usually closed by surgical staples and results in a gathering of the skin which is about ⅜ inch wide, ¼ inch high, and 8 to 12 inches long. Directly over the closed incision 32, there is placed a petroleum impregnated, sterile gauze material 34 which tends to adhere to the incision area and serves as a sterile barrier for the incision area. The surgeon will typically lay 4 inch by 8 inch gauze pieces 36 on the knee to further protect the incision 32 and the petroleum impregnated gauze 34 thereon.

The leg and knee area would typically be prepared as seen in FIG. 2, even if the surgeon chose not to include any means for reducing the temperature in the surgical area. In such situations, the area would be further dressed with A.B.D. pads, wrapped with an expandable gauze material roll, and then wrapped from the toe to the groin with an ace bandage for providing compression to the entire leg area. However, as mentioned hereinabove, some surgeons and post-operative teams have recognized the advantages of installing the fluid circulating blankets 10 in the knee area for proper cooling during the post-operative procedure. The prior art method, as discussed hereinabove, included an installation in the most simple and basic form on a relatively small leg. With the preferred blanket 10 being about 5 inches by 10 inches and the sterile gauze pieces about 4 inches by 8 inches, a single piece of gauze may simply be laid on the first side 12 of the fluid circulating blanket 10 when applied to the side of a small leg.

Figure 3:
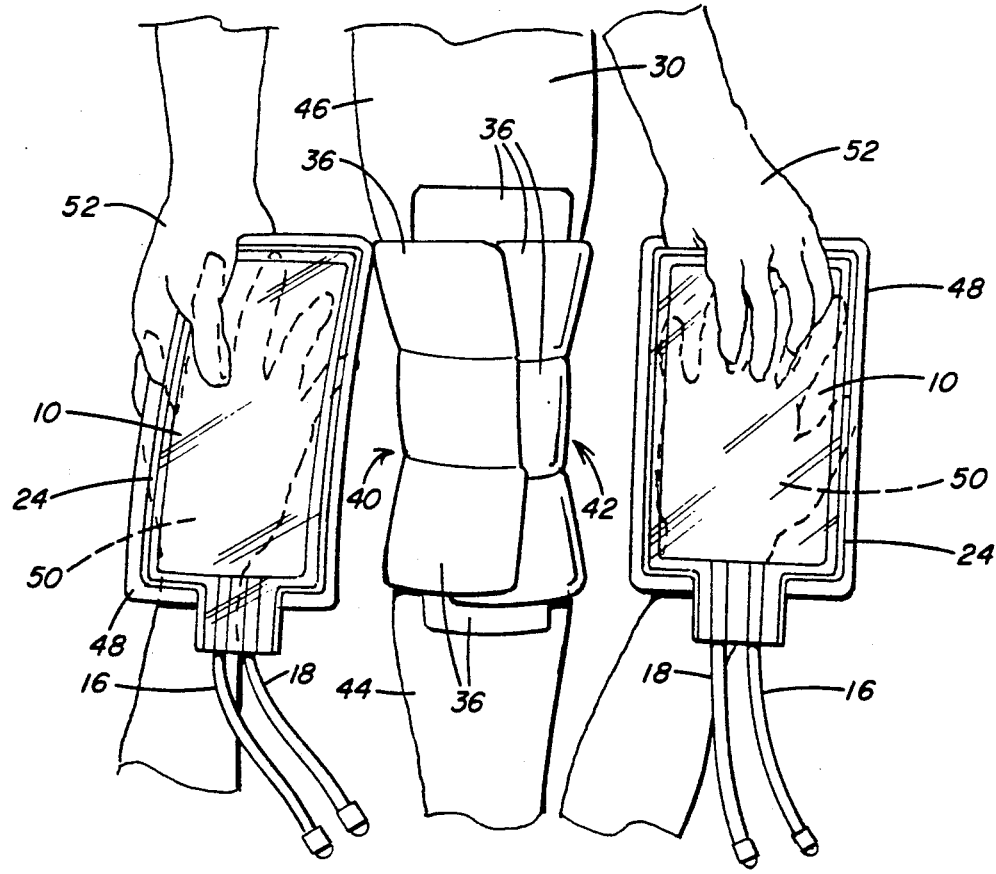
FIG. 3 is a schematic view demonstrating a prior art method of arranging the prior art blankets of FIG. 1 for alignment with the sides of the knee following knee surgery.

However, as seen in FIG. 3, with a larger leg 30, three 4 inch by 8 inch sterile gauze pieces 36 are laid in an overlapping manner on the lateral side 40 while three 4 inch by 8 inch sterile gauze pieces 36 are also laid in an overlapping manner on the medial side 42 of the knee area. Of course, the 4 inch by 8 inch gauze pieces must be individually removed from sterile peel packs. With the six overlying pieces 36 in position, an attending nurse removes two of the fluid circulating devices 10 with containers 24 thereabout from their respective sterile packages and two relatively larger A.B.D. pads from their respective sterile packages. As mentioned above, the A.B.D. pads are relatively thick and tend to provide insulation and cushioning on the outside of the fluid circulating blankets 10. The A.B.D. pads generally allow for swelling and expansion in the knee area and provide insulation to form a thermal barrier to direct the cold to the knee area. With the surgeon located at the toe end 44 of the leg 30 and an attending nurse at the upper end 46 of the leg, an A.B.D. pad 48 may be placed on the palm of each hand 50 of the surgeon. The fluid circulating blanket 10 and container 24 are then placed by the nurse 52 on the top of each of the A.B.D. pads 48 with each set of hoses 16, 18 extending toward the toe end 44 of the leg 30.

Figure 4:
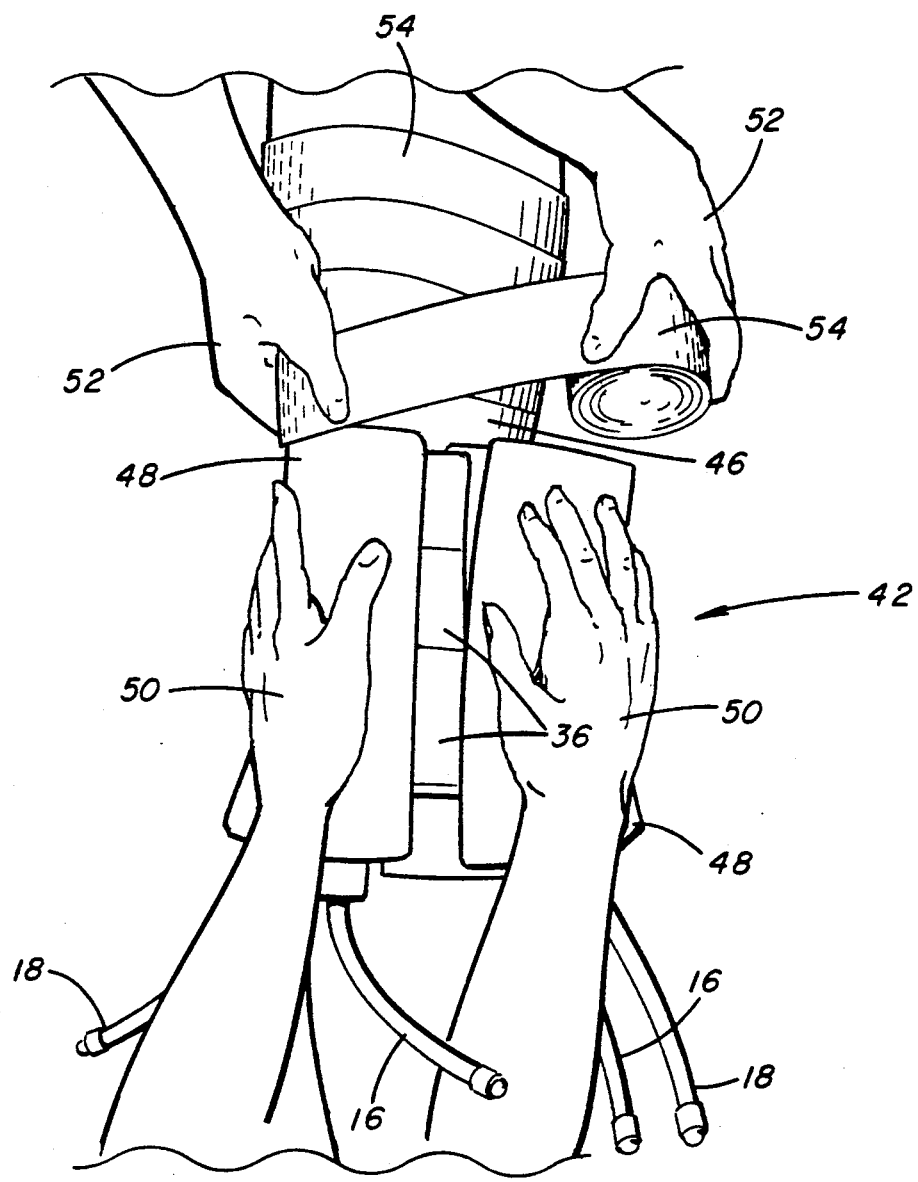
FIG. 4 is a schematic view of the prior art method of positioning the prior art blankets against the sides of the knee following knee surgery.

As seen in FIG. 4, the surgeon will, by hand, direct the containers 24 having the fluid circulating blankets 10 therein and the A.B.D. pads 48 against the lateral and medial sides of the knee area. With the containers 24, included blankets 10 and pads 48 properly positioned, the attending nurse will begin wrapping the leg 30 from the upper end 46 to the lower end 44 with a roll of stretchable, sterile gauze material 54. Wrapping in this manner to retain the pads 48 and blankets 10 against the sides of the knee area is very difficult because of the tendency to wrap and entrap the surgeons hands 50 inside of the wrapped gauze material 54. The schematic views shown in FIGS. 3 and 4 include a preferred alignment which is not easy to obtain during actual post-operative procedures. Although the blankets 10 and containers 24 tend to be flexible, they clearly resist bending around the curve of the leg 30 at both ends 44 and 46. The surgeon and nurse are required to work in a limited area and tend to get in each other's way. In fact, although not shown in FIGS. 3 or 4, additional operating attendants are frequently needed to raise and hold the leg 30 in order to facilitate the wrapping of the gauze material 54 around the leg. Additionally, it is also unclear from the schematic views just how cumbersome and awkward the extended hoses 16 and 18, even if included in a portion 25, tend to be while trying to maintain the fluid circulating blankets 10 in proper alignment at opposite sides of the incision area.

Figure 5:
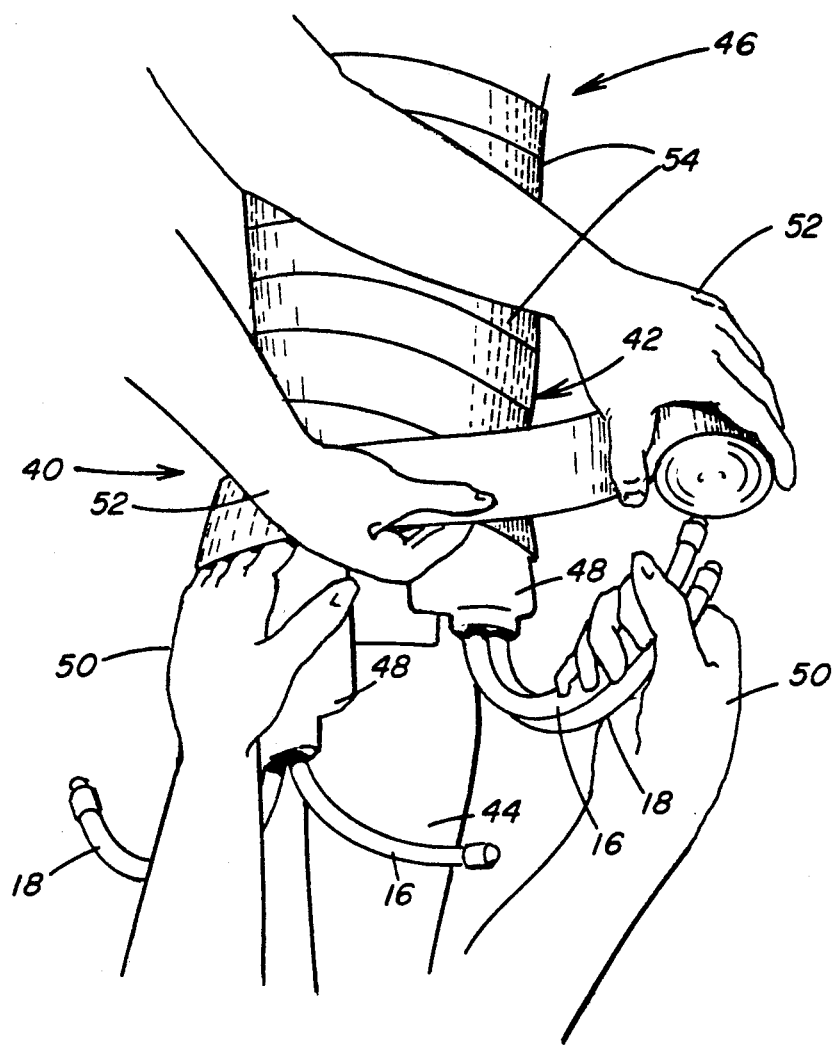
FIG. 5 is a schematic view demonstrating the difficulty of maintaining the prior art blankets in position by the prior art method of positioning.

Continued wrapping of the roll of gauze material 54 also requires attention to and alignment of the connection hoses 16 and 18 of each fluid circulating blanket 10. For example, as seen in FIG. 5, the wrapping to include the fluid circulating blanket 10 at the medial side 42 of the knee has been relatively effective so that the surgeon is no longer required to hold the blanket 10 at the medial side 42. However, unfortunately, by way of example, the blanket 10 at the lateral side 40 has been allowed to slip down toward the lower end 44 of the leg. Since the nurse is attempting to wrap the surgical area with the gauze material 54 in a manner which does not include the connection hoses 16, 18, one hand 50 of the surgeon will direct the connection hoses 16, 18 of the blanket 10 at the medial side 42 outwardly for continued wrapping while still trying to use the other hand 50 for properly maintaining the blanket 10 at the lateral side 40. Obviously, with continued wrapping and assuming that the hand 50 at the lateral side may be withdrawn, the connection hoses 16 and 18 of the blanket 10 at the lateral side 40 must also be held in an outward position as the wrapping toward the toe by the nurse continues. It should be noted that if the nurse were to drop the roll of gauze material 54 onto the operating floor during the wrapping, the wrapping would be removed and redone with a fresh sterile roll of material 54.

Of course, even with continued wrapping, as generally demonstrated in FIG. 5, the respective hoses 16, 18 of each of the blankets 10 may extend from the leg area in different positions and may be forwardly or rearwardly disposed on the leg to generally complicate a connection to the fluid circulating machine. Generally, it should be clear that the procedure described hereinabove is extremely complicated, cumbersome, awkward, and unreliable. The actual positions of the fluid circulating blankets 10 is not assured and the bending or dislocation of the connection hoses 16, 18 is very likely.

At first glance, different locations for the extended ends of the hoses 16, 18 would not seem to present any significant problems. However, some fluid circulating systems employ a single fluid discharge hose and a single fluid return hose. When two blankets are employed, a relatively small yoke fitting is attached to the end of each of the discharge and return hoses. Both inlet hoses 16 must be connected to the yoke fitting of the discharge hose and both outlet hoses 18 must be connected to the yoke fitting of the return hose. If the hoses 16 and the hoses 18 are poorly positioned, they may be bent or crimped as they are directed to the common yokes. The reduction or loss of normal flow could cause the entire system to be automatically turned off.

The complicated and cumbersome prior art method described hereinabove is repeatedly performed by skilled surgeons and attending nurses. However, some surgeons tend to allow physician's assistants and/or hospital technicians to attempt to install the blankets. Any problems experienced by surgeons would be increased if less skilled personnel are involved and the likelihood of successful and rapid placement would be significantly reduced.

In either case, after the complete wrapping of the gauze material 54, the leg, with the connection hoses 16, 18 again extending therefrom, is wrapped from the toe end 44 all the way to the groin end 46 with an ace bandage (not shown). The ace bandage maintains the gauze material 54, the A.B.D. pads 48, the fluid circulating blankets 10, the container 24 and the gauze pieces 36 in position, even if misaligned, and under compression until a time for changing the first dressing.

The post-operative control of temperature, with the fluid circulating blankets 10 connected to the temperature controlled, fluid circulating system described hereinabove, would typically continue for 3 to 5 days. After the 3 to 5 days, the post-operative team will inspect the surgical area and apply a fresh dressing. The ace bandage is removed and the wrapped gauze material 54 is gently cut apart in the mid-line area of the incision. The soiled petroleum impregnated gauze 34 is then removed for direct inspection of the incision 32. For this to be properly done, the blankets 10, including the containers 24, must be slightly pulled outwardly from the area of the incision, as the wrapped gauze material 54 is gently pulled back, in order to inspect the entire incision 32. Assuming there is no infection or undesired fluid build up in incision 32, a new strip of petroleum based gauze 34 is again applied to the incision 32. With additional gauze pieces 36 laid over the top thereof, the cut gauze material 54, the blankets 10, the containers 24 and the pads 48 are simply realigned to be adjacent the incision area as a new ace bandage is again wrapped about the entire leg. The ace bandage will again properly retain the gauze material 54, the pads 48, the blankets 10, the containers 24 and the gauze pieces 36 and 34 and produce compression on the leg as the blankets 10 are connected to the fluid circulating system for continued control of the temperature in the area of the knee surgery. From this discussion of the examination of the surgical area at the time of the first dressing change, it should be clear that the proper alignment of the pads 48 and blankets 10 are again critical in order to be able to ensure access to the incision 32.

The present invention is directed to improving the method and apparatus discussed hereinabove to more conveniently and reliably locate various fluid circulating blankets adjacent a surgical area. As will be seen, the preferred apparatus utilizes a support envelope for supporting a fluid circulating blankets therein and for entrapping condensation or moisture to prevent its collection on the patient. Proper use of the support envelopes facilitates positioning and alignment of the fluid circulating blankets 10 and insures that they are efficiently and effectively directed to the desired area to be cooled. Again, by way of example, it is appropriate to discuss how the preferred method and apparatus can be used to improve the recovery of a patient from knee surgery.

Generally, in the description hereinbelow, reference to the right or left side will be the right or left side as viewed in the figures rather than as applied to a patient.

As seen in FIG. 6A, a fluid circulating blanket 10 is disposed with the first side 12, which is to be directed to the area to be cooled, toward the viewer. The hoses 16, 18 are oriented in a downward position. A preferred support envelope 60 is formed about the blanket 10 with the inside surface 62 shown for alignment with the first side 12 of the blanket 10. A hose portion 61 of the envelope 60 extends along and tends to support the hoses 16, 18.

As seen in FIG. 6B, the fluid circulating blanket 10 is disposed with the second side 14 directed toward the viewer and, again, with the hoses 16, 18 extending downwardly therefrom. The support envelope 60 is shown in FIG. 6B with the outside surface 64 exposed and in alignment with the second side 14 of the fluid circulating blanket 10 with the outside surface 64 also extending through the portion 61.

With the fluid circulating blanket 10 having dimensions of about 5 inches by 10 inches, the preferred support envelope 60 has outside dimensions (approximately 5.5 inches by 10.5 inches) which are slightly larger than but correspond to the outer dimensions of the fluid circulating blanket 10 for encasing the blanket 10 within the interior 65 thereof. The support envelope 60 is water-tight to be able to collect condensation and moisture in the interior 65 but includes additional features for proper support and positioning of the blanket 10 on the patient.

As best seen in FIG. 7, the support envelope 60 may include the inside surface 62 made of an inside layer 68 of a thin plastic material and an outside layer 63 of a batiste or similar material which can be directly placed on the skin of the patient but is sufficiently thin and non-insulating to allow effective heat removal by the blanket 10. The outer layer 63 of the inside surface 62 may preferably be formed of a polyester waffle material which is non-irritating, allows the skin to breath, but tends to prevent the growth of bacteria.

The outside surface 64 of the support envelope 60 may be formed of an inside layer 68 of the thin plastic material and outer layers of a polypropylene or other foam material with a loop material laminated thereon. The polypropylene or other foam material of an intermediate layer 67 can provide insulation to retain the cold in the area of the blanket 10 for more effective reduction of the temperature in the surgical area. However, the preferred outside surface 64 would include the layer 67 made of a polypropylene felt material which is totally inert, hypo-allergenic and tends to prevent the growth of bacteria therein. Although the polypropylene felt material provides better insulation than the foam material, neither is intended to allow air to move freely therethrough. The outer surface is preferably provided an outer layer 69 of brushed-pile nylon or polyester on the outside thereof for connection with various hook tab or strip means in a manner described hereinbelow.

As seen in FIGS. 6A, 6B and 7, the inside surface 62 and the outside surface 64 of the support envelope 60 are joined together at edge sealing 66 which extends around the peripheral edge of the support envelope 60 and hose portion 61 with only a small opening 61a for the exit of the ends of the hoses 16, 18. R. F. sealing or some other heat sealing means can be used to join the edges at 66 to basically seal the union of the layers 63, 68, 67, and 69 to provide the sealed interior 65.

To form the support envelope 60, the blanket 10 is completely formed to include the hoses 16, 18. With the layers 68 and 63 positioned at the first side 12 and the layers 68, 67 and 69 positioned at the second side 14, the edges 66 are sealed to encase the blanket 10 in the support envelope 60 and the hoses 16, 18 in the hose portion 61 as the ends extend through the opening 61a.

The envelope 60 has many features which are not provided by the container 24 of FIG. 1. The envelope 60 includes the layer 63 to provide a proper surface for use against the patient. The insulating layer 67 insures that heat or cold is properly directed to the patient to improve the operation of the overall temperature controlled, fluid circulating system and promote rapid healing of the patient. As will be seen, the outer layer 69 provides a means for properly positioning the envelope 60 and enclosed blanket 10 against the desired area of the patient.

With better insulation for the blanket 10, when cold fluid is circulated through the blanket 10, an increased amount of condensation is likely to be formed. Since the envelope 60 may be directly placed against the patient, the retention of more condensation or moisture within the interior 65 may be required than was typically experienced by use of the container 24 alone. As a result, the layers 68, which specifically retain the moisture within the interior 65, are also more critical. With the likelihood of more condensation or moisture, the preferred support envelope 60 includes a long hose portion 61 to locate the opening 61a remote from the major portion of the blanket 10 and the area of the body to be cooled.

As will be discussed hereinbelow, with the possibility of tearing the prior art container 24 or a major leak in a blanket 10, the selection of the plastic material for the container 24 can tend to be a compromise. If the plastic material were too thick, it could prevent proper heating or cooling of the patient. Generally, the containers 24 have been made of lighter plastic material and have not been capable of retaining fluid at the operating pressure of the fluid circulating system to which the blanket is connected.

With the use of the heavier material of layers 63, 67 and 69, the plastic layers 68 of the preferred envelope would be generally protected and much less likely to tear. Still further the support provided by the additional layers 63, 67 and 69 may allow the plastic material of layers 68 to be sufficiently strong to be able to retain fluid, which may accidentally leak from a blanket, at a higher pressure than was possible with the container 24.

It is also significant that the hose portion 61 of the envelope 60 is configured different from the hose portion 25 of the container 24. With the preferred hose portion 61 also formed of the combined layers 63, 68, 67, and 69, the hose portion 61 has substantial integrity and is capable of firmly supporting the hoses 16, 18 extending therethrough. Support of the hoses 16, 18 in this manner, tends to prevent their being accidentally bent or crimped to restrict or prevent the flow of the fluid therethrough.

In a preferred form for convenient use following knee surgery, two blankets 10, respectively enclosed within two support envelopes 60, are provided. They are connected to each other by connection strap means in the form of two sterile straps 72. Each of the straps 72 includes a VELCRO hook tab 74 at each end thereof.

Figures 8, 9:
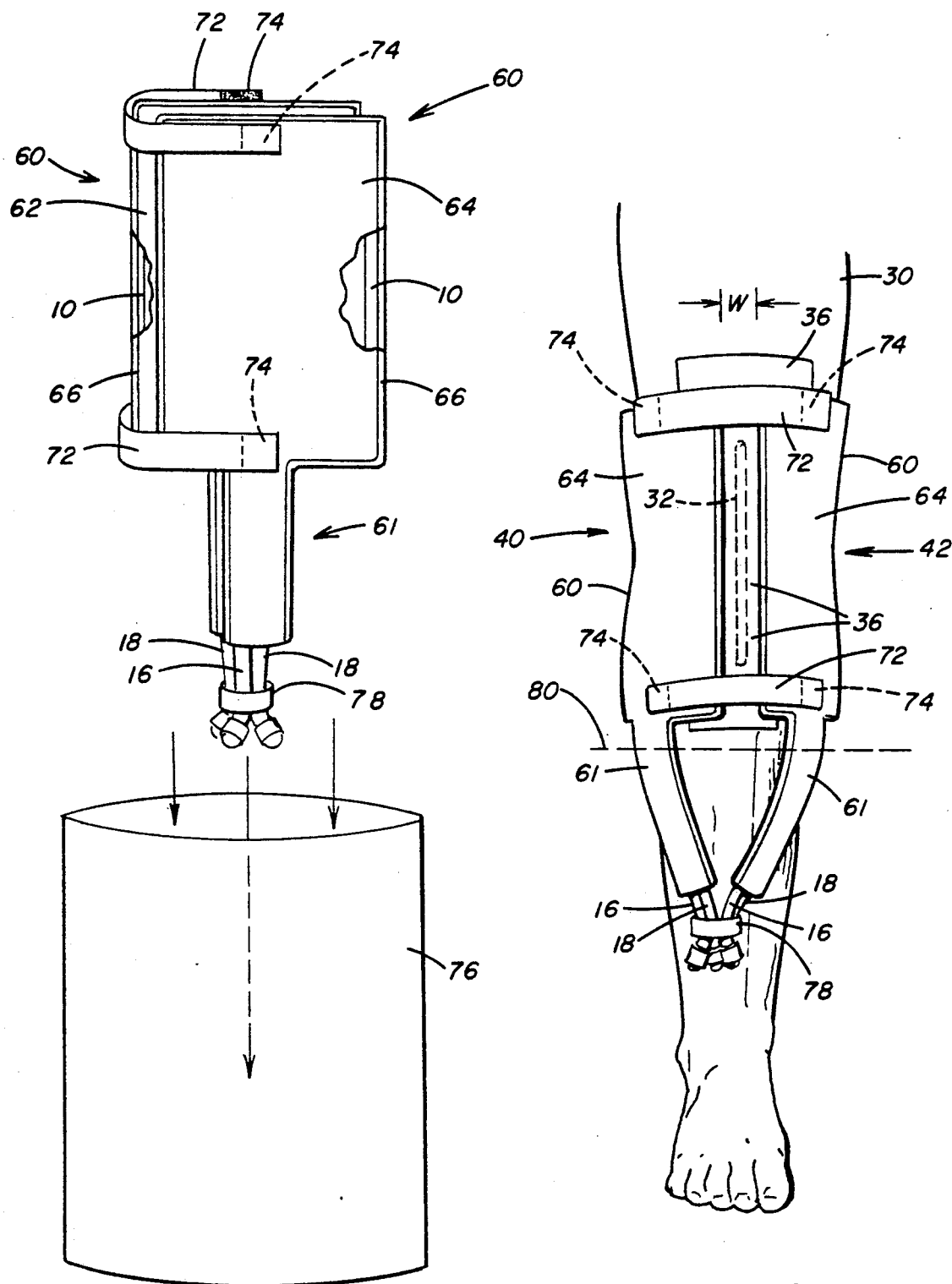
FIG. 8 is a perspective view of two support envelopes of FIGS. 6A, 6B and 7 joined together for insertion into a package in preparation for sterilization.
FIG. 9 is a schematic view of the knee area following the preparation step of FIG. 2 in which the preferred support envelopes, having blankets therein, are aligned with the opposite sides of the knee.

As best seen in FIG. 8, the two envelopes 60 are connected together by the straps 72 with the respective hoses 16, 18 of the blanket 10 extending toward the same direction. The hook tabs 74 at the ends of the straps 72 are adapted to adhere to the brushed-pile or loop surface on the outer layer 69 of the outside surface 64 of each of the support envelopes 60.

To package the combined support envelopes 60 with the blankets 10 therein, the envelopes 60 will be folded together and inserted in a container or package 76. Prior to packaging, the extended ends of both sets of hoses 16, 18 are joined together by rubber band means 78 or the like. As will be seen, this is not intended to simply facilitate installation in the package 76 but will directly contribute to improve positioning and alignment of the support envelopes 60 during the post-operative procedure. With the package 76 (whether a single or double configuration) properly sealed with the support envelopes 60 and the blankets 10 therein, the entire package and contents are preferably sterilized with ETO gas.

As seen in FIG. 9, the surgery to a knee is completed and prepared in the same manner as shown in FIG. 2. The incision 32 has been closed and the gauze 34 and the two gauze pieces 36 positioned directly over the incision 32. With the package 76 opened in the operating room by an attending nurse, the support envelopes 60 are directly positioned about the incision 32. The hoses 16, 18 from each blanket 10 extend down the leg 30 of the patient. However, the extended ends of the hoses 16, 18 are retained together by the rubber band means 78.

With the leg 30 in a horizontal position following surgery, the support envelopes 60 will tend to remain in position by gravity as they respectively support the blankets 10 therein. With proper positioning of the combined support envelopes 60, one strap 72 will be disposed above the area of incision 32 and the other strap 72 will be disposed below the incision area 32. Although the two support envelopes 60 are, for packaging purposes, joined together in the general manner as shown in FIGS. 8 and 9, the width W of the aperture between the upper edges of the envelopes 60 can be selectively adjusted by the surgeon by relocating the hook tabs 74 on each of the straps 72 until the desired width W is obtained.

The preferred method and apparatus eliminates a separately formed and less reliable container 24, many of the sterile gauze pieces 36, and the need for applying the A.B.D pads 48. The functions of these components are more readily, conveniently and reliably provided by the inside surface 62 and the outside surface 64 of each of the support envelopes 60. As a result, positioning the support envelopes 60 in the manner shown in FIG. 9 prepares the knee area for the wrapping of the leg with the sterile gauze roll material 54.

It should be obvious, from the positioning shown in FIG. 9, that gravity will generally cause the two blankets 10 to be properly positioned respectively at the lateral side 40 and the medial side 42. Actual holding and positioning by the surgeon or the nurse is not really necessary. Interestingly enough, the use of the rubber band means 78 can further assist gravity to insure proper positioning of the envelopes 60 and blankets 10. As the hoses 16, 18, joined at the rubber band means 78, are slightly bent upwardly to lie on the top part of the lower leg of the patient, their natural resilience will tend to cause the blankets 10 and the support envelopes 60 thereabout to lie closely against the upper surface of the leg.

The wrapping of the gauze material 54 is significantly simplified with the blankets 10 are retained within the envelopes 60 in the manner as shown. The lower corners or edges may be adjusted by the surgeon or nurse to lie against the lower sides of the leg 30 as wrapping continues down through the incision area 32. However, the attention required by the surgeon or nurse is quite insignificant when compared to the type of support and bending needed for the prior art positioning of the blankets 10 described hereinabove. In fact, the straps 72 positively insure that the upper corners of each blanket 10 are properly bent and properly positioned about the leg in a manner that was almost impossible to obtain with the prior art procedure.

Although not shown in FIG. 9, wrapping of the support envelopes 60 through the knee area with the gauze material 54 will continue to a location indicated by the dotted line 80. When the wrapping proceeds to the line 80, both the envelopes 60 and the blankets 10 therein are firmly positioned and secured. The hoses 16, 18 and surrounding hose portion 61 can then be bent upwardly from the leg 30 to allow wrapping of the material 54 downwardly toward the foot with each of the hoses 16, 18 and the hose portion 61 exposed for access to the ends thereof. The bending and positioning of the hoses 16, 18 is simplified by the use of the rubber band means 78. Because the blankets 10 are aligned in equal positions at opposite sides of the knee by the envelopes 60, the general length of the hoses 16, 18 would be about equal. The common bending at the line 80 allows them to extend from the wrapping with approximately the same length for eventual attachment to the overall fluid circulating system. It should be noted, as seen in FIG. 5, that the prior art method of installing the blankets 10 adjacent the knee area might have required that only one set of hoses 16, 18 be positioned outwardly of the leg while wrapping of the other blanket 10 proceeds with its particular hoses 16, 18 continuing to extend downwardly beside the lower portion of the leg. Later, these hoses 16, 18 must also be bent outwardly for the remainder of the wrapping. The preferred method and apparatus has eliminated separate wrapping and separate bending of the hoses to simplify their positioning and insure that the ends of the hoses and the end of the hose portion of the envelope will be accessible. Of course, the convenient positioning of the hoses will also simplify the wrapping of the ace bandage from the toe to the groin in order to apply the desired compression on the leg during the recovery period. As will be seen, locating the opening 61a outwardly of the ace bandage also allows convenient access for the removal of any condensation or moisture from the interior 65 of the envelope 60 if required.

The preferred method and apparatus as shown in FIG. 9 will also facilitate the examination of the incision area 32 at the first dressing change after about 3 to 5 days. With the surgeon having selected the width W, access to the incision 32 is generally assured. The upper edges of the support envelopes 60 and blankets 10 are sufficiently pliable to allow tucking and replacement of the gauze pieces 34. In any case, the wrapping with an ace bandage after the first dressing change is clearly simplified by the presence of the straps 72 which maintain the corners of the support envelopes 60 in general alignment about the leg 30.

The method and apparatus described hereinabove is clearly the preferred. However, as indicated in the discussion of the prior art, the thermal blankets are available from a number of different sources. The preferred method of providing blankets for a knee surgery includes forming the two support envelopes respectively around two blankets, joining the two envelopes together, inserting them in a common package and then sterilizing the overall package. However, an alternative method for the post-operative application of the blankets might require each blanket and support envelope to be provided in a different package and with the sterile straps and/or sterile rubber band means provided in their own package. In the operating room, the envelopes and blankets would be removed from their respective packages by an attending nurse. An attending nurse would then install the straps and apply the sterile rubber band means to the ends of the hoses.

Figure 10:
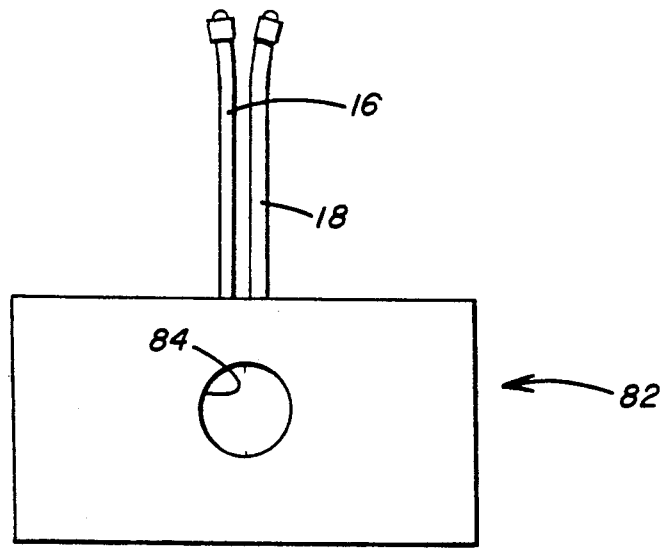
FIG. 10 is a plan view of another prior art fluid circulating blanket.

As clearly demonstrated hereinabove, the preferred use of blankets after a knee surgery includes two such blankets which are about 5 inches by 10 inches. However, as indicated in the prior art discussion, an increasing number of blanket configurations are being provided for special applications. As seen in FIG. 10, one such blanket 82 is about 8 inches by 12 inches and has a circular hole or opening 84 with a 2¼ inch diameter located in the center thereof. The blanket 82 is said to be capable of being utilized following knee surgery or elbow surgery. The opening 84 in the center of the blanket 82 is intended to relieve pressure on and prevent direct contact with the incision in the knee or elbow after surgery. However, as indicated hereinabove, surgery to the knee does not include an incision which is simply located at the knee. The incision may be 8 or more inches long. The entire length is preferably maintained free of any abrasive contact during recovery. The small circular hole 84 in the blanket 82 could result in undesired contact and significantly complicates examination of the incision after the operation.

Figure 11:
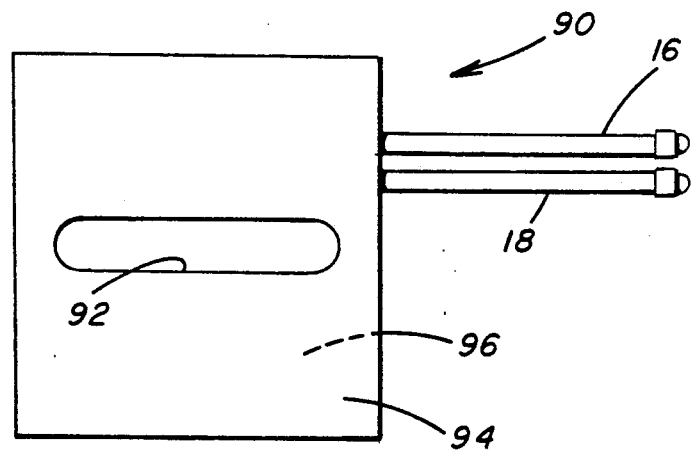
FIG. 11 is a simplified view of an improved fluid circulating blanket.

As seen in FIG. 11, an improved fluid circulating blanket 90 is configured to provide an alternative to the configuration of FIGS. 6A and 6B through 9. The blanket 90 has a length of about 10 inches and a width of about 12 inches to generally provide the same overall dimensions as the two blankets 10 discussed hereinabove. However, the blanket 90 includes a central elongated opening 92 which is about 8 inches long and about 1.5 inches wide. A single inlet hose 16 and exit hose 18 would be capable of providing cool fluid to both sides of the blanket 90.

Obviously, the blanket 90 could be employed postoperatively in the same general manner as the separate blankets 10 in the prior art manner as shown FIGS. 3 through 5. If used instead of two separate blankets, the blanket 90 would clearly be easier to align with the incision 32 and easier to maintain in position by a surgeon. Although, again, gravity would assist in the positioning of both sides of the blanket 90 respectively at the lateral and medial sides of the knee, the surgeon would still be needed to properly position, support and align the additional gauze pieces 36 and the A.B.D. pads 48. Accordingly, an overall preferred configuration would utilize some type of preferred support envelope to eliminate the need for the gauze pieces 36 and A.B.D. pads 48. The general configuration of the support envelopes 60 would not appear to be appropriate for the blanket 90 because of the need to provide an opening in alignment with the central opening 92 therein.

Figure 12:
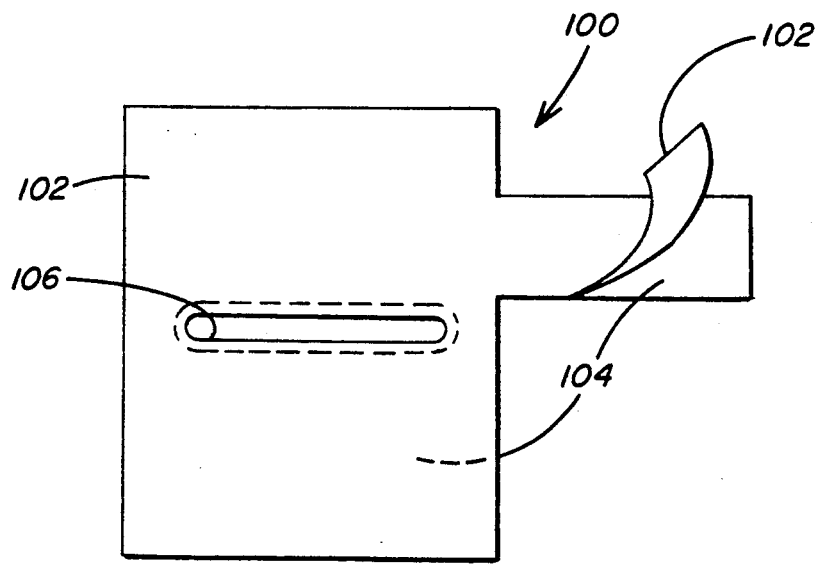
FIG. 12 is a simplified view of a preferred support envelope for installation on the improved fluid circulating blanket of FIG. 11.
Figure 13A:
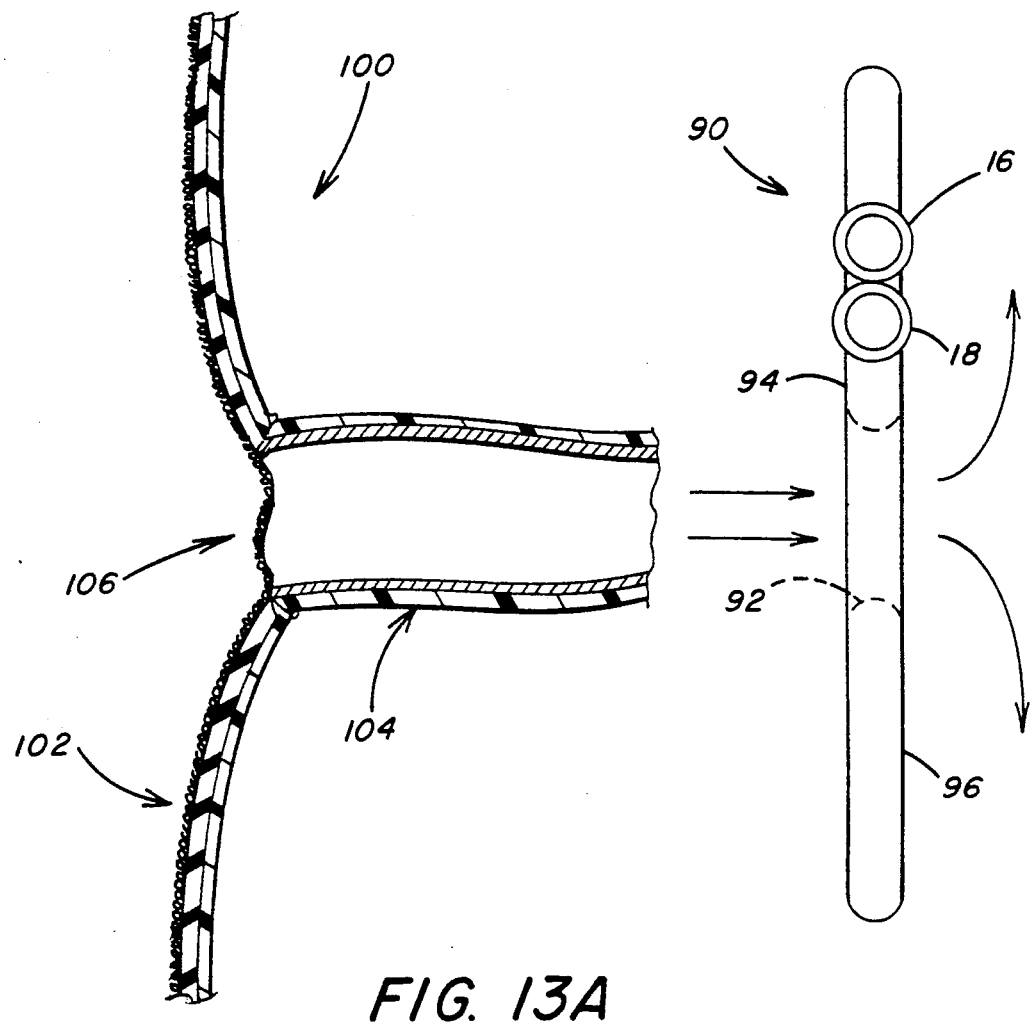
FIG. 13A is a side view of the support envelope of FIG. 12 demonstrating the installation of the support envelope on the fluid circulating blanket of FIG. 11.
Figure 13B:
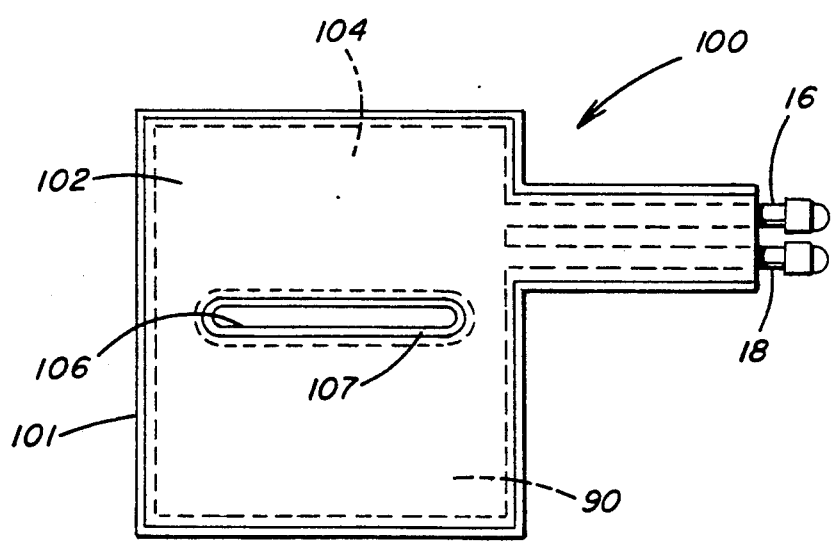
FIG. 13B is a view of the support envelopes of FIG. 12 completely formed with the blanket of FIG. 11 therein.

As seen in FIGS. 12, 13A and 13B one possible support envelope configuration 100 for the blanket 90 would include an outside surface 102 which is again preferably formed of an inside layer of plastic material with outer layers of foam or felt material with a loop material laminated thereon. The inside surface 104 is again preferably made of an inside layer of plastic material with a layer of batiste, polyester or similar material for direct placement against the skin in a non-insulating manner. However, the preferred inside surface 104 and the outside surface 102 are initially only joined by blind stitching together at the peripheral edge of a centrally positioned opening 106 in the support envelope 100.

Joining of the inside surface 104 and the outside surface 102 at the opening 106 in the preferred support envelope 100 with the edges turned inwardly results in a smooth, abrasive free joining which is preferred even though it is not initially sealed. Accordingly, as seen in FIG. 13A, in order for the support envelope 100 to be installed on a blanket 90, the inside surface 104 is simply gathered at the region of the opening 106 for insertion through the opening 92 of the envelope 90. With the second side 94 of the blanket 90 properly aligned with and in contact with the interior of the outside surface 102, the gathered inside surface 104 is repositioned and straightened for alignment with the first side 96 of the blanket 90. As seen in FIG. 13B, the edge 107 at the opening 106 and the peripheral edged 101 of the envelope 100 are permanent joined by sealing, after the blanket is installed, in order to be able to retain condensation or moisture within the interior of the envelope 100 during use. Positioning on the patient's body could again be provided by separate straps having hook tabs at the ends thereof for connection to and adjustment on the outer surface 102. For example, if positioned against the lateral and medial sides of the knee, a simple strap at the top end and a strap at the bottom end could be used to join the respective outer edges of the support envelope 100 as it is folded toward the backside of the leg.

The support envelope 100 and enclosed blanket 90 are equally appropriate for use following an elbow surgery. Again, the alignment of the openings 92, 106 longitudinally along the arm insures that there will be no contact with the incision area when the arm is being bent at the elbow.

It should be noted that during post-operative recovery, it is not uncommon for the leg 30 of the patient to be connected to a motion producing machine. Typically, such a motion producing machine will periodically cause movement of the leg from a 0 degree to a 30 degree bend at the knee during the first day of recovery. The range of motion will typically be increased by about 10 degrees each day until discharge. The objective is to produce a bending motion of 90 degrees at the knee prior to discharge to enable the patient to be able to properly stand from a seated position and to climb stairs during continued recovery in the hospital or at home. However, with a clear objective of mobility in the knee, it is significant that the fluid circulating blankets 10 and blanket 90 are not directly on the area of incision 32 and are not directed to the popliteal area behind the knee. Locating a fluid circulating blanket in the popliteal area or the incision area 32 might create significant abrasions in either area during the controlled movement of the knee. The resulting abrasions would be extremely undesirable and could be quite damaging.

Abrasion of the incision area is highly likely with the prior art blanket 82. Because of the likelihood of misalignment of the blankets 10 by the prior art method of FIGS. 3 through 5, abrasion of the incision area and/or the popliteal area behind the knee is also likely. In fact, the prior art devices of U.S. Pat. Nos. 4,026,299 and 4,523,594 would clearly damage both the incision area and the popliteal area because of the method taught therein for wrapping around the knee.

Figure 14:
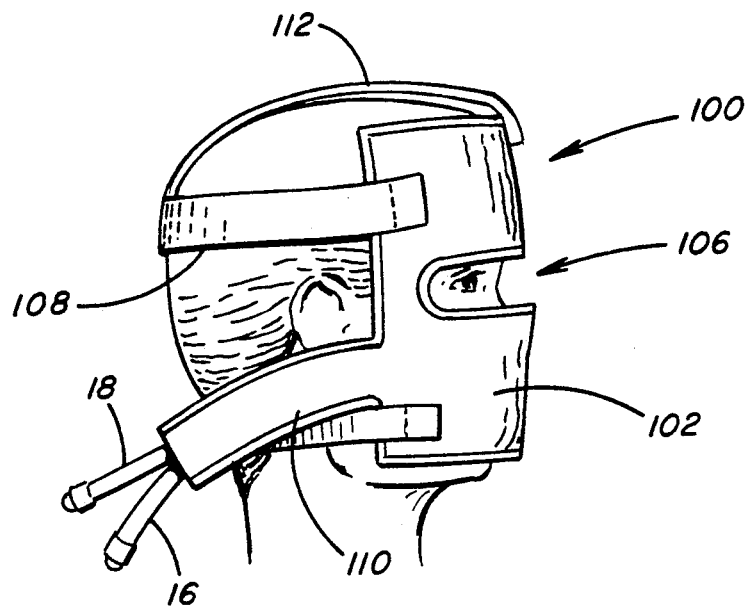
FIG. 14 is a perspective view of one selective positioning of the support envelope and blanket of FIG. 13B on the facial area of a patient.

It has also been found that the preferred blanket 90 and envelope 100 offer additional opportunities for controlling temperature in the facial area following various types of surgery. As seen in FIG. 14, an upper strap 108 including hook tabs, such as that described hereinabove, and a lower strap 110 including hook tabs can be employed to respectively secure the upper and lower areas of the support envelope 100 to cause the first side of the blanket 90 to be retained against the facial area. An additional strap 112 can be extended across the top of the head of the patient to further insure that the blanket 90 and envelope 100 will be retained at the desired position on the face. Although not shown, it will be apparent to those skilled in the art that additional gauze material or ace bandages could be applied to further maintain the blanket 90 and support envelope 100 in position throughout post-operative recovery. In any case, the straps 108, 110, and 112 would generally retain the blanket 90 and support envelope 100 in proper alignment.

Figure 15:
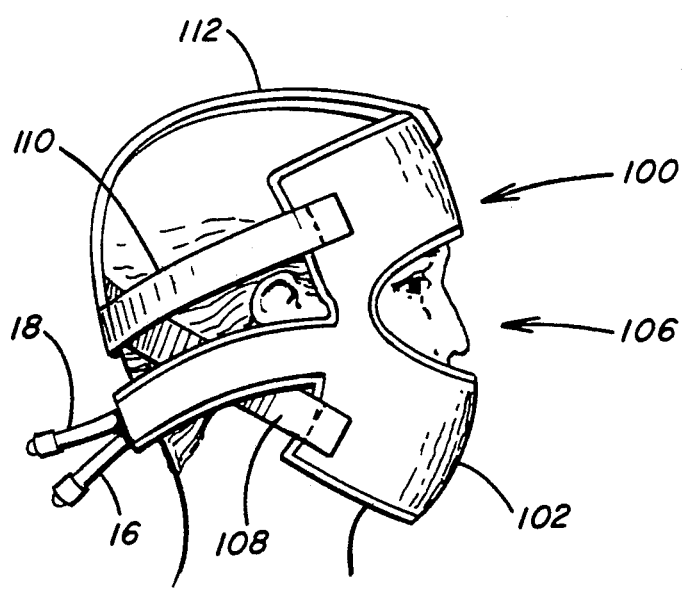
FIG. 15 is a perspective view of another selective positioning of the support envelope and blanket of FIG. 13B on the facial area of a patient.

Although the configuration and alignment shown in FIG. 14 clearly allows the patient to see, the general spacing around the nose also allows the patient to breathe. However, as seen in FIG. 15, should the surgeon determine that the entire nose should be free of contact with the blanket 90, the same preferred blanket 90 can be configured to increase the widths of the openings 92, 106 around the eyes and nose. As seen, a crossing of the straps 108 and 110 produces a curved contour to the blanket 90 and support envelope 100 to relieve both the eye and nose area of the patient. A similar strap 112 can be positioned across the top of the head of the patient to again prevent undesired downward movement of the blanket 90 and insure that the width of the openings are maintained as desired.

Figure 16A:
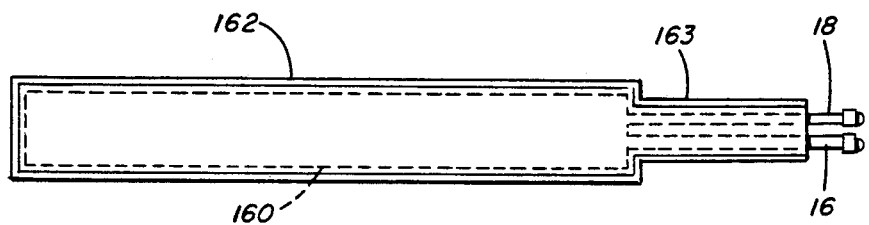
FIG. 16A is a simplified view of a preferred support envelope including another fluid circulating blanket.

Although the fluid circulating blanket 10 discussed hereinabove was particularly appropriate for the knee surgery, the same sized blanket can be used in other areas of the body for post-operative procedures. In fact, the preferred method of post-operatively controlling a temperature in various areas of the body following surgery can be basically performed by the use of the blanket 10, a blanket 160 (FIG. 16A), which is 3 inches by 20 inches, or a blanket area 190 (FIG. 19), which is 10 inches by 14 inches. By supporting at least one of the blankets 10, 100, 160, or 190 in respective specifically designed support envelopes, numerous areas of the body can be conveniently, effectively, and reliably cooled to post-operatively reduce the pain, swelling and blood loss of the patient after surgery.

As mentioned hereinabove, blanket 100 can be employed for knee, elbow, eye, nose or mouth surgery. As will be seen, preferred apparatus of the present invention can also be used to support the 5 inch by 10 inch blanket 10 following hip, shoulder, thigh, calf, wrist and humerous surgery, in addition to the knee surgery as described. The 3 inch by 20 inch blanket 160 can be properly supported on a patient following face, neck, ear, elbow, ankle and groin surgery. The blanket area 190 is preferably directed to the back of a patient.

Figure 16B:
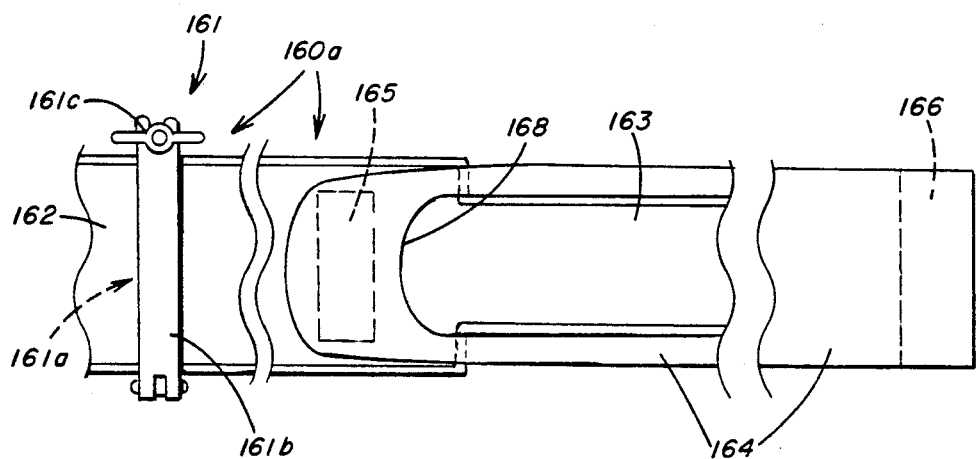
FIG. 16B is an enlarged view of a preferred connecting strap for use with the support envelope of FIG. 16A and including other features of the invention.

As seen in FIGS. 16A through 16G, fluid circulating blanket 160 is 3 inches wide by 20 inches long. Again, the blanket 160 includes a supply hose 16 and an exit hose 18. The blanket 160 is supported, according to the present invention, in another preferred support envelope 162 including a hose portion 163 and having similar inside surface material and outside surface material as the support envelopes described hereinabove. As seen in FIG. 16B, a preferred strap 164 is employed to basically secure the envelope 160 to the desired area of the body. The strap is about 15 inches long and has a hook tab 166 at one end and a hook tab 165 at the other end. An opening 168 in the strap 164 adjacent the hook tab 165 is provided for the hoses 16, 18 and the hose portion 163 to be extended therethrough as the hook tab 165 is initially installed on the outside surface of the envelope 162.

Figures 16C, 16D, 16E:
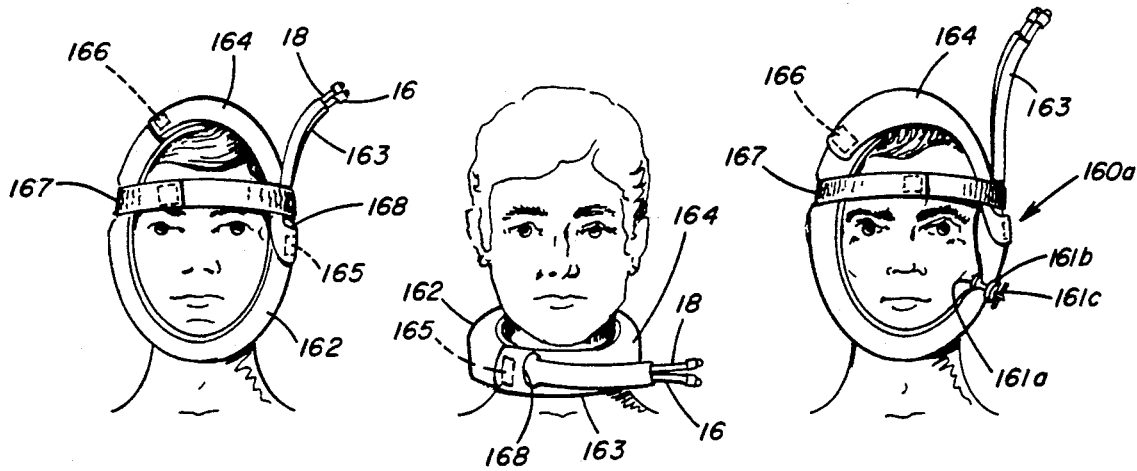
FIGS. 16C through 16H include views of the support envelope of FIG. 16A on various areas of the body.

As seen in FIG. 16C the preferred envelope 162 can be installed around the face of a patient for controlling the temperature of the facial area following various forms of cheek or jaw surgery. It should be clear to the surgeon and the recovery team that the wrapping of the support envelope 162 about the head of a patient could be adjusted for patient comfort and for convenient positioning of the hoses 16, 18 for eventual connection to the overall fluid circulating system. With the support envelope 162 and blanket 160 therein being wrapped about the facial area of the patient, the strap 164 extends beyond the hoses 16, 18 and hose portion 163 so that hook tab 166 on the end thereof can be snugly attached to the outside of the support envelope 162 at any appropriate location therealong. To further maintain the support envelope 162 in a proper position on the facial area of the patient, a sterilized strap 167 is provided. The preferred sterilized strap 167 is about 36 inches long and about 1¼ inches wide and includes a hook tab at each end thereof. The backside of the strap 167 is again formed of brushed-pile or loop material to which the hook tabs can be readily secured. After the support envelope 162 is positioned about the face, one end of the strap 167 is attached to the outside of the support envelope 162. With the strap wrapped about the patient's head, the other end of the strap 167 can be secured at any region along the backside of the strap 167 in order to retain the support envelope 162 in position.

As seen in FIG. 16D, the same support envelope 162 with a blanket 160 therein can be employed to control the temperature of a patient in the neck area. The support envelope 162 is wrapped about the neck with the strap 164 again extending beyond the hoses 16, 18 and hose portion 163 for attachment to the outside surface of the support envelope 162 at an appropriate location for maintaining the blanket 160 against the neck area. Clearly, the wrapping configuration is adjustable for various patients and can be selectively positioned for locating the hoses 16, 18 for convenient attachment to the fluid circulating system.

As seen in FIG. 16E, the same basic configuration of FIG. 16B can be employed for controlling the temperature following some forms of ear surgery. A slight repositioning of the support envelope 162 with the blanket 160 therein will allow the blanket to be directed to the ear area rather than the facial area of FIG. 16C. Again, the sterile strap 167 can be used to maintain the support envelope 162 in position over the ear.

If the arrangements shown in FIGS. 16C, 16D or 16E result in the blanket 160 covering too large an area of the patient, a clamping means 161, as generally shown in FIG. 16B, can be selectively positioned along the length of the blanket 160 away from the hoses to limit the cooling area to that portion 160a adjacent the hoses. Proper positioning of the envelope 162 would allow only the cool area or portion 160a, as established by the clamping means 161, to be aligned with the desired area. The clamping means 161 may include a lower, cushioned bar 161a for alignment with the inside surface of the envelope and blanket and a top bar 161b hinged to one end of the cushioned bar 161a. A releasable connection means 161c at the other end of the bars 161a and 161b allows selective movement of the clamping means 161 along the length of the support envelope 162. When the connection means 161c joins the ends of the bars 161a and 161b together, the bars tend to squeeze the envelope and blanket therebetween to limit the area 160a (as seen in FIG. 16E) of the blanket 160 to which the fluid is supplied by the hose 16 and from which the fluid is discharged by the hose 18.

Figure 16F:
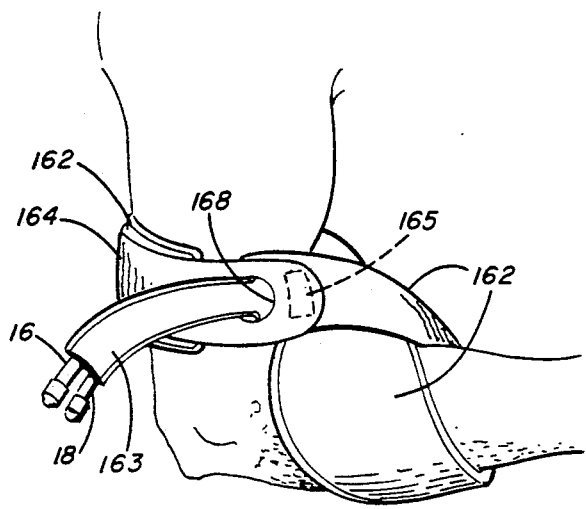

As seen in FIG. 16F, the support envelope 162 can be employed to direct the fluid circulating blanket 160 to the elbow area with a figure-8 design for use following some elbow surgery. Again, the hook tab 166 will adhere to the outside of the envelope 162 and the hoses 16, 18 and hose portion 163 can be selectively, conveniently directed away from the patient for connection to the overall fluid circulating system.

Figure 16H:
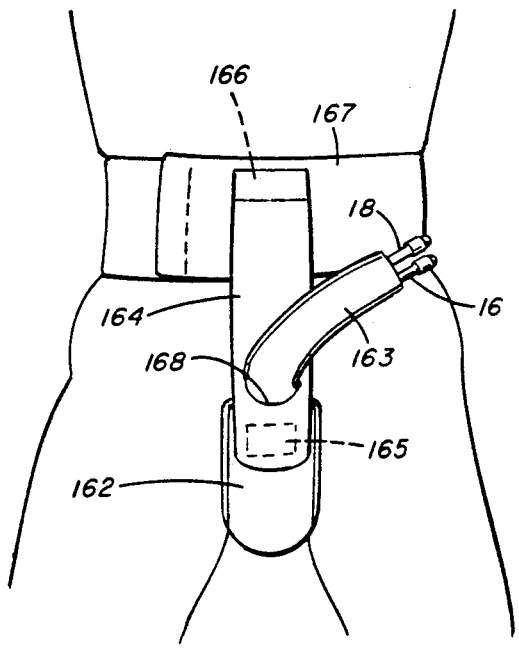
Figure 16G:
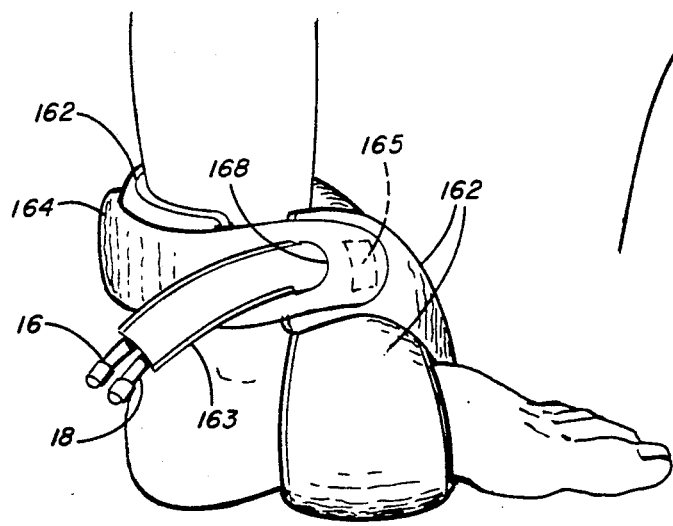

A similar figure-8 configuration, as seen in FIG. 16G, can be employed for some ankle surgery with the support envelope 162 being secured in the same manner as used on the elbow in FIG. 16F.

As seen in FIG. 16H, the preferred support envelope 162 can be utilized to direct the fluid circulating blanket 160 to the groin area following surgery. However, in this case, a preferred sterilized universal torso support 169 is employed. The preferred torso support 169 is about 5½ inches wide and about 60 inches long. The universal torso support 169 would again include the brushed-pile or loop material on the back surface thereof. The inside surface would again have a hook strip region about 1½ inches wide extending across the width of the support at least one end thereof. To secure the support envelope 162 in the groin area, the end thereof which is remote from the hoses 16, 18 is positioned at the back of the patient to allow the blanket 160 to be extended through the groin area toward the front of the patient. The universal torso support 169 is preferably wrapped around the waist of the patient to entrap the remote end of the support envelope 162 at the back of the patient. The hook tab 166 on the end of the strap 164 can be adjusted to the frontal region of the universal torso support 169 to complete the securing of the support envelope 162 in the groin area. The hoses 16, 18 are positioned conveniently in the stomach area of the patient for connection to the overall fluid circulating system.

As seen in FIGS. 17A through 17F, the support envelope 60 can be utilized for post-operatively reducing the temperature in the area of the shoulder, thigh or humerus following surgery. A strap 170 which is about 20 inches long and about 5½ inches wide and two straps 175, which are about 12 inches long, are adapted for supporting the 10 inch by 5 inch fluid circulating blanket 10 within the envelope 60. A first end 171 of the strap 170 and a second end 172 of the strap 170 each includes hook tabs 173 at the corners thereof. The strap 170 also includes a series of slits 174 generally disposed toward the end 171. With the hoses 16, 18 and hose portion 61 extending through a selected slit 174, depending on the overall length desired, the hook tabs 173 at the end 171 are secured to the outside surface 64 of the envelope. Hook tabs 176 are also provided at the ends of each strap 175 for adjustable attachment to the outside surface 64 of support envelope 60.

Figure 17A:
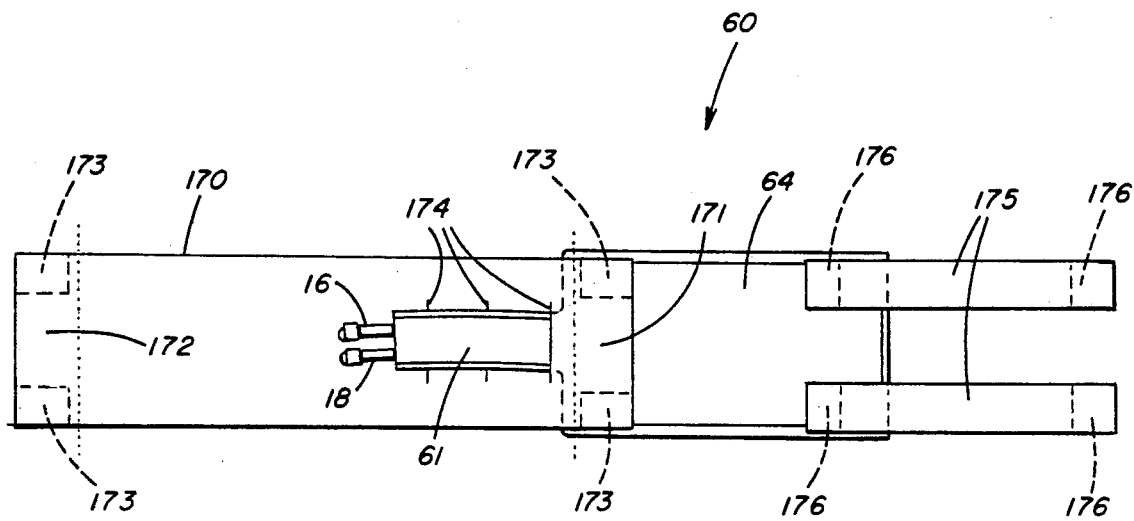
FIG. 17A is a simplified view of another support envelope for supporting a fluid circulating blanket therein.
Figures 17B, 17C, 17D:
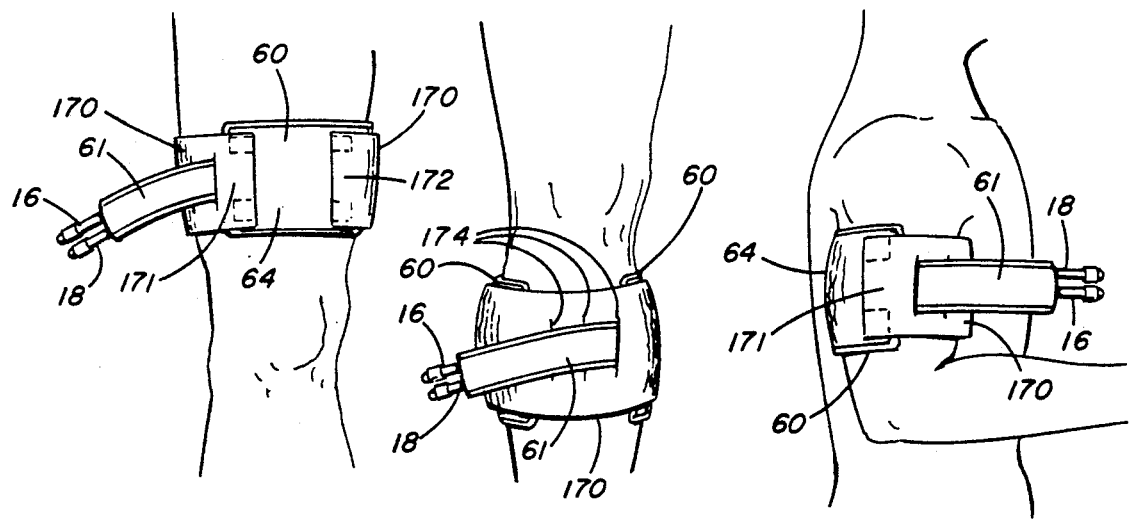
FIGS. 17B through 17F include schematic views of the support envelope of FIG. 17A as it is applied to various areas of a patient.

As seen in FIG. 17B, 17C, and 17D, the support envelope 60 can be respectively positioned for controlling the temperature in the thigh area, calf area or humerus area of a patient following surgery. In each case, the straps 175 have been removed and the strap 170 is used alone for securely positioning the support envelope 60. The end of the envelope 60 remote from the hoses 16, 18 is initially placed against the surface of the patient to allow the support envelope 60 and the blanket 10 therein to be wrapped about the appropriate area of the patient. The hook tabs 173 at the end 172 of the strap 170 can be adjustably secured to the outside of the support envelope 60 for proper support on the patient.

Figure 17E:
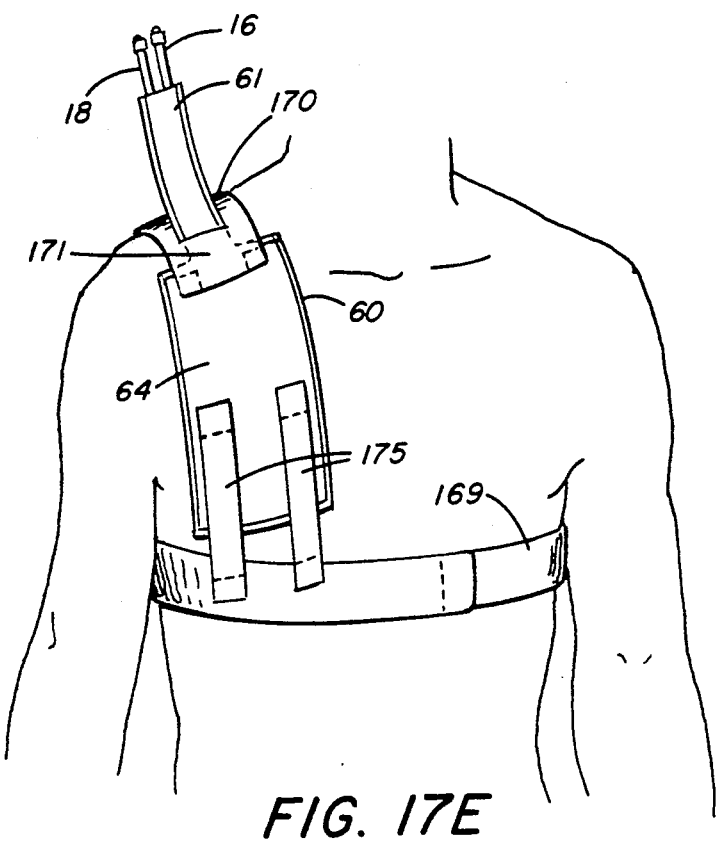

As seen in FIG. 17E, the support envelope 60 and straps 170, 175 can be employed for shoulder surgery with the additional use of the universal torso support 169. The universal torso support 169 is wrapped about the lower chest area of the patient with the hook tabs 176 of the strap 175 attached to the frontal area of the universal torso support 169 while the hook tabs at the end 172 of the strap 170 are attached to the rear area of the universal torso support 169.

Figure 17F:
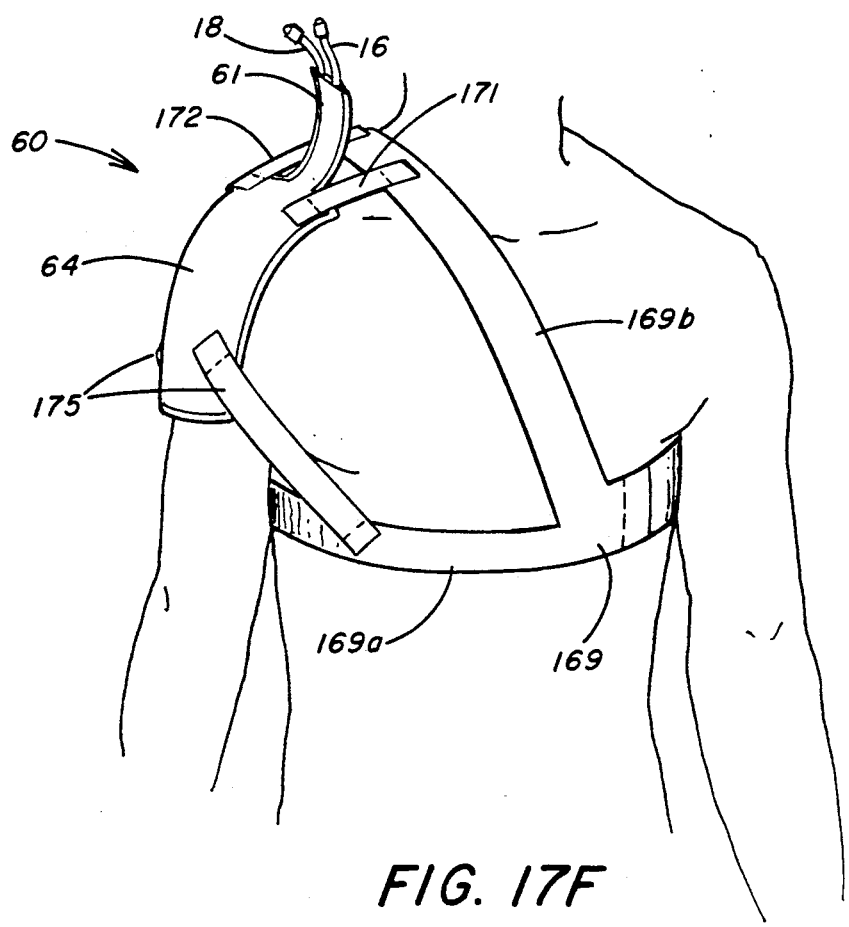

As seen in FIG. 17F, the shoulder surgery may require a different configuration for the direction of the support envelope 60 to the shoulder area. In this case, the operating team will remove the strap 170 from the envelope 60 and cut the basic strap 170 as indicated at the dotted lines 177 to form two small straps from the ends 171, 172 and further divide the strip 172 into two halves 172a and 172b as indicated by the dotted lines at 178. Again, the universal torso support 169 is generally wrapped around the lower chest area of the patient. However, a longitudinal cut along the center of the support 169 allows a lower part 169a to remain at the chest while an upper part 169b extends from the frontal area of the basic support 169 and over the shoulder to the back of the basic support 169. The envelope 60 is positioned on the shoulder with one strap 175 directed to the front of the patient for attachment to the lower part 169a of the universal support 169 and the other strap 175 directed to the back side of the patient for attachment to the part 169a of the support 169. The two small strips 171 and 172 are connected to the outside of the support envelope 170 at each corner adjacent the hose portion 61 for attachment to the upper part 169b of the support 169.

As seen in FIGS. 18A through 18D, a preferred support envelope 180 having an alternative form is formed about a blanket 10 having the same 5 inch by 10 inch dimensions. The support envelope 180 is preferably about 18 inches long and about 5½ inches wide to extend beyond the basic blanket 10 at both ends thereof. The inside surface 182 and outside surface 184 are basically formed of the same multiple layers of material as discussed hereinabove. However, two intergral straps 185 are formed at one end to extend along the opposite sides of the hose portion 186. Hook tabs 187 have been secured to the inside surface 182 at the ends of each integral strap 185 either before or after formation of the envelope 180 about the blanket 10. An extended end 183 extends beyond the other end of the blanket 10. Peripherial sealing 181 about the entire edge of the support envelope 180 during formation about the blanket 10 maintains all of the layered material together at all of the edges of the envelope 180 except at the open end of the hose portion 186. Further, interior sealing 188 defines the sealed interior of the envelope 180 which directly surrounds the blanket 10 and hoses 16, 18 to prevent moisture of fluid from collecting in the straps 185 or the extended end 183 of the envelope.

As seen in FIGS. 18B and 18C, the support envelope 180 is respectively employed on the forearm and on the wrist of a patient following surgery. The support envelope 180 and blanket 10 are simply wrapped about the forearm or the wrist area with the hook tabs 187 of each strap 185 being adjustably connected to the outside surface 184 of the support envelope 180.

As seen in FIG. 18D, the preferred support envelope 180 can be used to direct the blanket 10 to the hip following various hip surgeries. For use in the hip area, the sterilized universal torso support 169 is again wrapped about the waist of the patient. An additional sterile strap 189 is about 3 inches wide by 36 inches long and again includes a hook tab at one end thereof. The additional strap 189 is adjustably wrapped and secured around the thigh area of the patient. With the support 169 or the strap 189 overlying the extended end 183 of the support envelope 180, the straps 185 of the support envelope 180 are secured with the hook tabs 187 to the outside of the other support 169 or strap 189.

Finally, by way of example, as seen in FIG. 19, an alternative support envelope 192 can be integrally formed to include a fluid circulating blanket area 190. The blanket area 190 is similar to those described hereinabove but includes outside dimensions of 10 inches by 14 inches to define the area of the fluid circulating channels or passages. The blanket area 190 is centrally supported in the support envelope 192 and includes hoses 16, 18 extending to one side thereof. A pair of integrally formed straps 195 with installed hook tabs 197 extend from the blanket area 190 at each side of the hoses 16, 18 and a narrowing side portion 196 extends from the other side of the blanket area 190. With the blanket area 190 positioned against the back of the patient, the side portion 196 is initially wrapped around to the front of the body and the two straps 195 extended about the other side of the body as the hook tabs 197 are secured to the outside surface 191 of the envelope 192 at the portion 196. The support envelope 192 could be applied to the patient in either direction to specifically direct the hoses 16, 18 to either side of the patient for convenient connection to the overall fluid circulating system.

From the view as seen in FIG. 19, it can be seen that a support envelope, like that of FIG. 18A, could be formed about an initially formed blanket including the hose 16, 18 and having the outside dimensions of 10 inches by 14 inches. With a surrounding support envelope, like that of FIG. 18A, a hose portion would be included to again extend around the hoses 16, 18. The only real difference in configuration would be the size of the side straps and side portion.

The support envelope 192 includes the outside surface 191 and the inside surface 193 which are similar to those of the support envelopes described hereinabove. However, there is included no light plastic material for simply forming a sealed interior for surrounding a separate blanket member. Instead, a heavier sheet plastic material is disposed beneath the layer of material for being directed against the skin and beneath the insulating layer and brushed-pile layer for forming the outside of the envelope 192. The heavier sheet plastic material is the type which is used to form a basic blanket member. Accordingly, when the layers are joined to form the integral support envelope, the blanket area 190 is formed in the same manner as the other blankets described hereinabove to include the fluid channels or passages (not shown) which are connected to the hoses 16, 18. The layered inside surface 193 forms the first side of the blanket area 190 and the insulated layered outside surface 191 forms the second side of the blanket area 190.

The support envelope 192 would probably be more difficult and more expensive to form than the support envelopes discussed hereinabove because of the more complicated and expensive equipment which is typically needed to form the blankets having internal channels or passages. The blanket area 190 would be configured to withstand the operating pressure of the fluid circulating system but have an inside surface for contacting the patient, an outside surface which is insulated, and integral means for securely positioning the blanket area 190 against the area of the patient. Obviously, as described, the support envelope 192 includes no specific means for collecting condensation or moisture or for collecting small amounts of fluid if the blanket portion 190 were to leak.

However, with the use of the multiple layers of material at the inside surface and the outside surface of the support envelope 92, it would be possible to include another piece of thin plastic material to lie against the heavier plastic material needed for specifically forming the blanket area 190. With a proper design for joining the additional layer of thin plastic material to the heavier plastic material of the blanket area, it would be possible for some moisture or a small amount of leaking fluid to be collected between the two layers of plastic material if desired.

Figure 20:
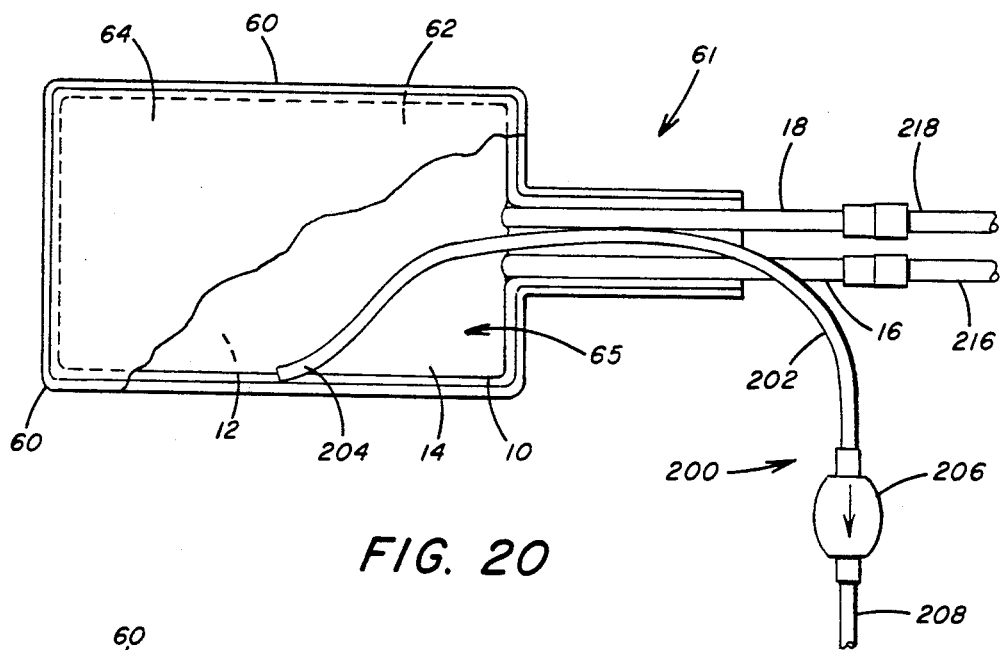
FIG. 20 is an enlarged view of another feature of the invention for use of the preferred support envelope in a fluid circulating system.

From the description of the preferred support envelopes provided hereinabove, it should be clear that with proper insulation there is an increased likelihood of the collection of condensation or moisture within the interior 65 of the various envelopes, such as support envelope 60. As seen in FIG. 20, the invention includes means for removing condensation, moisture, or small quantities of fluid which may collect in the interior 65 of the envelope 60. A collection of moisture or fluid could interfere with the transfer of heat or could leak from the interior 65 of the support envelope 60 through the hose portion 61 to cause considerable discomfort to the patient.

Accordingly, as seen in FIG. 20, the invention includes a fluid removal system 200 having a long suction hose 202 which is capable of being extended through the hose portion 61 of the blanket 60, generally between the hoses 16, 18. The end 204 of the suction hose 202 is positioned within the interior 65 of the envelope 60 for drawing the moisture or fluid into the suction hose 202. The preferred fluid removal system 200 includes a hand operated pumping device 206 having check valve means at each side thereof for reducing the pressure in the suction hoses 202 to draw the moisture or fluid from the interior 65 for discharge at the discharge side 208 of the fluid removal system 200. Clearly, with a slow collection of moisture or fluid within the interior 65 of the support envelope 60, periodic operation of the pumping device 206 by an attending nurse would tend to prevent an undesired collection of fluid within the interior 65.

Still further, as mentioned hereinabove, the various layers forming the preferred support envelope 60 may add sufficient integrity and reinforcement to the support envelope 60 to allow a collection of fluid therein which may generally approach operating pressure if there were a leak in the enclosed blanket 10. Clearly, the prior art container 24 would not have been able to sustain any pressure even remotely approaching the operating pressure of the fluid circulating system. However, with the reinforced surfaces of the preferred support envelope 60, it is possible that a leak of fluid from the blanket 10 could result in a collection of a substantial amount of fluid within the interior 65 of the envelope 60.

Figure 21:
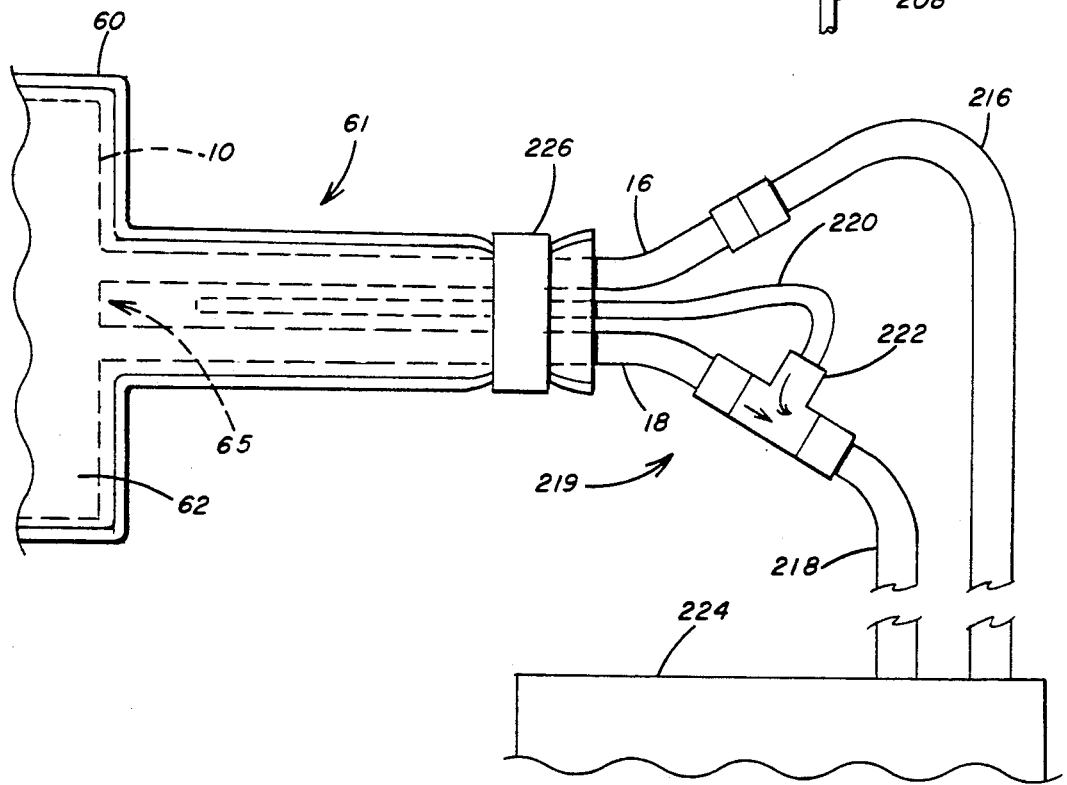
FIG. 21 is a fragmentary view of an alternative feature of the invention for use with the preferred support envelope in conjunction with a fluid circulating system.

While, a substantial leak of the type described would interfere with heat transfer between the blanket 10 and the patient, it is perhaps more significant that the fluid would tend to fill up the interior 65 of the envelope 60. As seen in FIG. 21, the present invention includes means for preventing an undue collection of warmer fluid within the interior 65 of the envelope 60 even if it is generally capable of sustaining the operating pressure of the fluid circulating system. To remove the warmer fluid from the interior 65, an alternative fluid removal system 219 of the invention includes a suction hose 220 which is connected to a one-way check valve device 222. The check valve device 222 is connected between the exit hose 18 and the return hose 218 of the fluid circulating system 224. During operation of the fluid circulating system 224, cool, pressurized fluid will be provided to the supply line 216 for entrance into the blanket 10 through the hoses 16. If the blanket 10 were to develop a leak, fluid collecting in the interior 65 of the envelope 60 would migrate toward the hose portion 61. An adjustable clamping device 226, including deformable sealing means about the interior surface thereof, is preferably installed about the hose portion 61 and the hoses 16, 18 and the suction hose 220 therein.

With the end of the suction hose 220 located within the interior of the hose portion 61, fluid would be capable of flowing into the suction hoses 220. The cool fluid provided through the hose 16 would be at the system operating pressure. Leaking fluid within the interior 65 of the support envelope 60 would be at a lower pressure. The return fluid through the exit hose 18 and the return line 218 to the fluid circulating machine 224 would also be at a lower pressure. Proper installation of the one-way check valve system 222 in a fitting between the exit hose 18 and return hose 218 could produce a sufficient drawing pressure on the suction hose 220 to allow the fluid within the interior 65 of the support envelope 60 to be drawn back into the fluid circulating system 224.

It should be clear, from the description of the various embodiments of the invention as provided hereinabove, that various support envelopes could be provided for conveniently positioning various sizes of fluid circulating blankets to a patient to control various areas of the body following surgery. Clearly, other alterations could be made to the specific support envelope configurations while still being able to support the blanket on the patient and to eliminate the use of many gauze pieces for disposition against the body and/or pads which were heretofore needed for proper insulation and cushioning. It should be noted from the detailed description of the prior art method of applying the blankets following knee surgery that the preferred support envelopes for the support of the various blankets may be further secured and maintained on the patient by the use of the wrapped gauze material, ace bandages, or some other types of slings or body support elements. However, the use of the preferred support envelopes clearly facilitates positioning of the blankets on the patient and tends to insure proper positioning throughout use. If used for a post-operative period, the preferred support envelopes will, again, reduce the time that a patient is anesthetized and will eliminate any need for tape to be directly applied to the patient as sometimes occurred in the prior art method of directing the blankets to the desired area.

Clearly, various modifications and alterations to the preferred embodiments and the method described herein could be provided by those skilled in the art without departing from the scope of the invention as claimed. It should be recognized that the various support envelopes could be formed of laminated material to include plastic or other material at the interior side thereof for the retention of moisture and the outer layers being formed of other material. The batiste material and the insulating material with a brushed-pile or loop outer surface might be respectively laminated to the plastic material to form two integral piece of layered material for the edges to be sealed together to form the support envelope. Still further, it should be noted that some fluid circulating blankets presently employ insulating material which appears to be laminated to one side of the blanket. The preferred support envelopes including the blankets therein would eliminate the need for insulating material directly laminated to the blanket. This insulating material is again primarily for retaining the heat or cold in the desired area of the body. Finally, the availability of non-abrasive hook material for tabs or strips and/or the availability of other forms of hook accepting loop material that provides insulation could also result in further modifications of the specific embodiments shown herein while still being within the scope of the invention as claimed.

I claim:

1. Apparatus for use with a temperature controlled fluid circulating device, said apparatus for controlling a temperature of an area of a body, said apparatus comprising:
    a fluid circulating blanket;
    said fluid circulating blanket having a first side and a second side;
    said fluid circulating blanket having fluid connection hose means extending from one edge thereof;
    said fluid connection hose means including an extended end adapted to be connected to the fluid circulating device;
    a support envelope surrounding said fluid circulating blanket to enclose at least said first side and said second side within an interior of said support envelope;
    said support envelope including a waterproof inside surface adjacent said first side and a waterproof outside surface adjacent said second side of said fluid circulating blanket;
    said waterproof inside surface having means for preventing a passage of fluid therethrough and having outwardly disposed material for placement against the area of the body;
    said waterproof outside surface having means for preventing a passage of fluid therethrough and including insulation material; and
    said waterproof outside surface and said waterproof inside surface of said support envelope being sealed at peripheral edges thereof to cause said support envelope to be capable of collecting fluid within said interior of said support envelope.

2. The apparatus according to claim 1, wherein said waterproof inside surface includes an inward layer of waterproof material and said outwardly disposed material includes an outward layer of cloth material.

3. The apparatus according to claim 2, wherein said inward layer and said outward layer of said waterproof inside surface are joined at least at said peripheral edges of said support envelope.

4. The apparatus according to claim 3, wherein said waterproof material is sheet plastic material and said cloth material is a substantially non-insulating synthetic material.

5. The apparatus according to claim 1, wherein said waterproof outside surface includes an inward layer of waterproof material and at least one outward layer of said insulation material.

6. The apparatus according to claim 5, wherein said inward layer and said at least one outward layer of said waterproof outside surface are joined at least at said peripheral edges of said support envelope.

7. The apparatus according to claim 6, wherein said waterproof material is sheet plastic material and said insulating material is at least one of polypropylene foam material and polypropylene felt material.

8. The apparatus according to claim 1, further including adjustable retaining means for retaining said support envelope on the body with said waterproof inside surface thereof against the area of the body.

9. The apparatus according to claim 8, wherein said adjustable retaining means includes at least one hook connection element and said waterproof outside surface of said support envelope includes surface means for being releasably connected to said at least one hook connection element.

10. The apparatus according to claim 9, wherein said surface means includes at least one of brushed-pile material and loop material forming an outermost layer of said waterproof outer surface.

11. The apparatus according to claim 10, wherein said waterproof outer surface includes an inward layer of waterproof material, an intermediate layer is between said inward layer and said outermost layer, and said intermediate layer includes said insulating material.

12. The apparatus according to claim 1, wherein said support envelope includes a hose portion formed of an extension of said waterproof inside surface and an extension of said waterproof outside surface and said hose portion extends around said fluid connection hose means for support of said fluid connection hose means.

13. The apparatus according to claim 1, further including means for removing said fluid when said fluid is collected within said interior of said support envelope.

14. The apparatus according to claim 1, wherein said fluid circulating device and said support envelope are sterile.

15. An apparatus for use with a temperature controlled fluid circulating device, said apparatus for controlling a temperature of an area of a body, said apparatus comprising:
   a fluid circulating blanket;
   said fluid circulating blanket having a first side and a second side;
   said fluid circulating blanket having fluid connection hose means extending form one edge thereof;
   said fluid connection hose means including an extended end adapted to be connected to the fluid circulating device;
   said fluid circulating blanket having an elongated opening to define a first half and a second half of said fluid circulating blanket;
   a support envelope surrounding said fluid circulating blanket to enclose at least said first side and said second side within an interior of said support envelope;
   said support envelope including an inside surface adjacent said first side and an outside surface adjacent said second side;
   said support envelope including an elongated envelope opening in alignment with said elongated opening of said fluid circulating blanket;
   said inside surface and said outside surface being joined at least at an edge of said elongated envelope opening;
   means for securely positioning said support envelope, with said fluid circulating blanket therein, with said inside surface of said support envelope against the area of the body; and
   said inside surface and said outside surface being waterproof and being sealed at said edge and at a peripheral edge surrounding said fluid circulating blanket to cause said support envelope to be capable of collecting fluid within said interior of said support envelope.

16. The apparatus according to claim 15, wherein said means for securely positioning said support envelope includes adjustable retaining means for retaining said support envelope on the body,
   said adjustable retaining means includes means for adjusting a width of said elongated envelope opening and said elongated opening, and
   said means for adjusting is for selectively positioning said first half and said second half of said fluid circulating blanket in alignment with the area of the body.

17. The apparatus according to claim 15, wherein said inside surface of said support envelope includes an inward layer of waterproof material and an outward layer of cloth material.

18. The apparatus according to claim 17, wherein said waterproof material is sheet plastic material and said cloth material is a substantially non-insulating synthetic material.

19. The apparatus according to claim 15, wherein said outside surface of said support envelope includes an inward layer of waterproof material and at least one outward layer of insulation material.

20. The apparatus according to claim 20, wherein said waterproof material is sheet plastic material and said insulating material is at least one of polypropylene foam material and polypropylene felt material.

* * * * *